United States Patent
Dong et al.

(10) Patent No.: US 8,483,808 B2
(45) Date of Patent: Jul. 9, 2013

(54) METHODS AND SYSTEMS FOR CHARACTERIZING CARDIAC SIGNAL MORPHOLOGY USING K-FIT ANALYSIS

(76) Inventors: Yanting Dong, Shoreview, MN (US); Shijie Zhang, Cleveland, OH (US); Dan Li, Shoreview, MN (US); Yayun Lin, St. Paul, MN (US)

(*) Notice: Subject to any disclaimer, the term of this patent is extended or adjusted under 35 U.S.C. 154(b) by 306 days.

(21) Appl. No.: 12/879,147

(22) Filed: Sep. 10, 2010

(65) Prior Publication Data
US 2011/0077541 A1 Mar. 31, 2011

Related U.S. Application Data

(60) Provisional application No. 61/245,871, filed on Sep. 25, 2009.

(51) Int. Cl.
*A61N 5/0472* (2006.01)
*A61B 5/0452* (2006.01)

(52) U.S. Cl.
CPC .................. *A61B 5/04525* (2013.01)
USPC .............. 600/509; 600/515; 600/518

(58) Field of Classification Search
USPC ............ 607/25, 26; 600/508, 509, 515–518
See application file for complete search history.

(56) References Cited

U.S. PATENT DOCUMENTS

| | | |
|---|---|---|
| 4,023,564 A | 5/1977 | Valiquette et al. |
| 4,336,810 A | 6/1982 | Anderson et al. |
| 4,428,378 A | 1/1984 | Anderson et al. |
| 4,774,950 A | 10/1988 | Cohen |
| 4,865,036 A | 9/1989 | Chirife |
| 5,002,052 A | 3/1991 | Haluska |
| 5,107,850 A | 4/1992 | Olive |
| 5,158,092 A | 10/1992 | Glace |
| 5,176,137 A | 1/1993 | Erickson et al. |
| 5,181,511 A | 1/1993 | Nickolls et al. |

(Continued)

FOREIGN PATENT DOCUMENTS

| | | |
|---|---|---|
| EP | 0253505 | 1/1988 |
| EP | 0360412 | 3/1990 |

(Continued)

OTHER PUBLICATIONS

Goya-Esteban et al., ""A Review on Recent Patents in Digital Processing for Cardiac Electric Signals (I): From Basic Systems to Arrhythmia Analysis"", *Recent Patents on Biomedical Engineering*, 2:22-31 (2009).

(Continued)

*Primary Examiner* — Carl H Layno
*Assistant Examiner* — Eugene Wu
(74) *Attorney, Agent, or Firm* — Pauly, DeVries Smith & Deffner LLC

(57) ABSTRACT

A system and method for automatically analyzing a cardiac signal, including the step of providing an episode database on a computer storage medium including a plurality of episode data records of one or more patients. Each episode data record includes a cardiac signal from at least one data-generating device. The method also includes the step of selecting one or more of the N beats to be one or more beat templates, for at least a first cardiac signal having N beats. Another step is determining a value K for the cardiac signal using a computer system where K beat templates can represent all the N beats in the cardiac signal.

15 Claims, 16 Drawing Sheets

U.S. PATENT DOCUMENTS

| | | | |
|---|---|---|---|
| 5,217,021 A | 6/1993 | Steinhaus et al. | |
| 5,251,621 A | 10/1993 | Collins | |
| 5,270,457 A | 12/1993 | LaBella et al. | |
| 5,312,441 A | 5/1994 | Mader et al. | |
| 5,312,445 A | 5/1994 | Nappholz et al. | |
| 5,330,505 A | 7/1994 | Cohen | |
| 5,379,776 A | 1/1995 | Murphy et al. | |
| 5,398,183 A * | 3/1995 | Elliott | 600/509 |
| 5,425,749 A | 6/1995 | Adams | |
| 5,447,519 A | 9/1995 | Peterson | |
| 5,458,620 A | 10/1995 | Adams et al. | |
| 5,554,177 A | 9/1996 | Kieval et al. | |
| 5,725,559 A | 3/1998 | Alt et al. | |
| 5,755,737 A | 5/1998 | Prieve et al. | |
| 5,779,645 A | 7/1998 | Olson et al. | |
| 5,782,888 A | 7/1998 | Sun et al. | |
| 5,817,027 A | 10/1998 | Arand et al. | |
| 5,857,977 A | 1/1999 | Caswell et al. | |
| 5,893,882 A | 4/1999 | Peterson et al. | |
| 5,978,707 A | 11/1999 | Krig et al. | |
| 6,064,906 A | 5/2000 | Langberg et al. | |
| 6,151,524 A | 11/2000 | Krig et al. | |
| 6,178,350 B1 | 1/2001 | Olson et al. | |
| 6,192,275 B1 | 2/2001 | Zhu et al. | |
| 6,212,428 B1 | 4/2001 | Hsu et al. | |
| 6,221,011 B1 | 4/2001 | Bardy | |
| 6,223,078 B1 | 4/2001 | Marcovecchio | |
| 6,230,055 B1 | 5/2001 | Sun et al. | |
| 6,253,102 B1 | 6/2001 | Hsu et al. | |
| 6,266,554 B1 | 7/2001 | Hsu et al. | |
| 6,270,457 B1 | 8/2001 | Bardy | |
| 6,275,732 B1 | 8/2001 | Hsu et al. | |
| 6,277,072 B1 | 8/2001 | Bardy | |
| 6,280,380 B1 | 8/2001 | Bardy | |
| 6,289,248 B1 | 9/2001 | Conley et al. | |
| 6,308,095 B1 | 10/2001 | Hsu et al. | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,393,316 B1 | 5/2002 | Gillberg et al. | |
| 6,398,728 B1 | 6/2002 | Bardy | |
| 6,400,986 B1 | 6/2002 | Sun et al. | |
| 6,434,417 B1 | 8/2002 | Lovett | |
| 6,438,407 B1 | 8/2002 | Ousdigian et al. | |
| 6,438,410 B2 | 8/2002 | Hsu et al. | |
| 6,440,066 B1 | 8/2002 | Bardy | |
| 6,449,503 B1 | 9/2002 | Hsu | |
| 6,477,422 B1 | 11/2002 | Splett | |
| 6,480,734 B1 | 11/2002 | Zhang et al. | |
| 6,487,443 B2 | 11/2002 | Olson et al. | |
| 6,490,478 B1 | 12/2002 | Zhang et al. | |
| 6,564,106 B2 | 5/2003 | Guck et al. | |
| 6,611,713 B2 | 8/2003 | Schauerte | |
| 6,631,290 B1 | 10/2003 | Guck et al. | |
| 6,636,764 B1 | 10/2003 | Fain et al. | |
| 6,654,639 B1 | 11/2003 | Lu | |
| 6,684,100 B1 | 1/2004 | Sweeney et al. | |
| 6,708,058 B2 | 3/2004 | Kim et al. | |
| 6,731,982 B1 | 5/2004 | Kroll et al. | |
| 6,766,194 B1 | 7/2004 | Kroll | |
| 6,801,806 B2 | 10/2004 | Sun et al. | |
| 6,882,883 B2 | 4/2005 | Condie et al. | |
| 6,885,890 B2 | 4/2005 | Spinelli et al. | |
| 6,889,079 B2 | 5/2005 | Bocek et al. | |
| 6,909,916 B2 | 6/2005 | Spinelli et al. | |
| 6,922,585 B2 | 7/2005 | Zhou et al. | |
| 6,978,182 B2 | 12/2005 | Mazar et al. | |
| 6,980,861 B1 | 12/2005 | Kleine | |
| 7,031,764 B2 | 4/2006 | Schwartz et al. | |
| 7,031,771 B2 | 4/2006 | Brown et al. | |
| 7,076,289 B2 | 7/2006 | Sarkar et al. | |
| 7,103,404 B2 | 9/2006 | Stadler et al. | |
| 7,103,405 B2 | 9/2006 | Sarkar et al. | |
| 7,107,098 B2 | 9/2006 | Sharma et al. | |
| 7,129,935 B2 | 10/2006 | Mackey | |
| 7,130,677 B2 | 10/2006 | Brown et al. | |
| 7,130,678 B2 | 10/2006 | Ritscher et al. | |
| 7,184,815 B2 | 2/2007 | Kim et al. | |
| 7,228,173 B2 | 6/2007 | Cazares | |
| 7,242,978 B2 | 7/2007 | Cao et al. | |
| 7,277,747 B2 | 10/2007 | Cazares et al. | |
| 7,330,757 B2 | 2/2008 | Ostroff et al. | |
| 7,354,404 B2 | 4/2008 | Kim et al. | |
| 7,430,446 B2 * | 9/2008 | Li | 600/515 |
| 7,474,916 B2 | 1/2009 | Gutierrez | |
| 7,477,932 B2 | 1/2009 | Lee et al. | |
| 7,480,529 B2 | 1/2009 | Li | |
| 7,558,623 B2 | 7/2009 | Fischell et al. | |
| 7,653,431 B2 | 1/2010 | Cazares et al. | |
| 7,706,866 B2 | 4/2010 | Zhang et al. | |
| 7,725,184 B2 | 5/2010 | Cazares | |
| 7,729,762 B2 | 6/2010 | Sun et al. | |
| 7,818,056 B2 | 10/2010 | Kim et al. | |
| 7,894,893 B2 | 2/2011 | Kim et al. | |
| 7,908,001 B2 | 3/2011 | Li et al. | |
| 7,917,196 B2 | 3/2011 | Zhang et al. | |
| 7,933,651 B2 | 4/2011 | Cazares et al. | |
| 8,140,153 B2 | 3/2012 | Cazares | |
| 8,185,195 B2 | 5/2012 | Kim et al. | |
| 2005/0137641 A1 | 6/2005 | Naughton et al. | |
| 2006/0074331 A1 | 4/2006 | Kim et al. | |
| 2006/0281996 A1 | 12/2006 | Kuo et al. | |
| 2007/0142736 A1* | 6/2007 | Cazares et al. | 600/515 |
| 2008/0071182 A1 | 3/2008 | Cazares et al. | |
| 2008/0125824 A1 | 5/2008 | Sauer et al. | |
| 2008/0161703 A1 | 7/2008 | Houben et al. | |
| 2009/0131996 A1 | 5/2009 | Li | |
| 2011/0166613 A1 | 7/2011 | Li et al. | |

FOREIGN PATENT DOCUMENTS

| | | |
|---|---|---|
| EP | 0467695 | 1/1992 |
| EP | 0547733 | 6/1993 |
| EP | 0709112 | 5/1996 |
| EP | 0801960 | 10/1997 |
| WO | WO-9840122 | 9/1998 |
| WO | WO-0170104 | 9/2001 |
| WO | WO-0224276 | 3/2002 |
| WO | WO-03034917 | 5/2003 |
| WO | WO-03047690 | 10/2003 |
| WO | WO-03092810 | 11/2003 |

OTHER PUBLICATIONS

Gold, Michael R. et al., "Advanced Rhythm Discrimination for Implantable Cardioverter Defibrillators Using Electrogram Vector Timing and Correlation", Journal of Cardiovascular Electrophysiology Nov. 2002, vol. 13, No. 11; pp. 1092-1097.

Mercando, et al., "Measurement of Differences in Timing and Sequence Between Two Ventricular Electrodes as a Means of Tachycardia Differentiation", PACE Nov.-Dec. 1986, Part II, vol. 9, 1069-1078 (abstract only).

Unknown, "Vitality 2 Implantable Cardioverter Defibrillator System Guide", Guidant Corporation 2004, Cover pages and pp. 3-15 to 3-19.

Lake, et al., "Sample entropy analysis of neonatal heart rate variability", Am. J. Physiol Regul Integr Comp Physiol. 2002, vol. 283; cover pg and pp. R789-R797.

Richman, Joshua S. et al., "Physiological time-series analysis using approximate entropy and sample entropy", Am. J. Physiol Heart Circ. Physiol. 2000, 278: H2039-H2049.

Dubin, "Rapid Interpretation of EKG's", Cover Publishing Company, 6th Edition 2000, p. 334-345.

"File History for U.S. Appl. No. 11/312,279", as of Dec. 26, 2012, Entitled "Discriminating Polymorphic and Monomorphic Cardiac Rhythms Using Template Generation," filed Dec. 20, 2005 (300 pages).

"File History for U.S. Appl. No. 13/048,582", as of Dec. 26, 2012, Entitled "Automatic Multi-Level Therapy Based on Morphologic Organization of an Arrhythmia," filed Mar. 15, 2011 (213 pages).

"PCT International Preliminary Report on Patentability from International Application No. PCT/US2006/047215", corresponding to U.S. Appl. No. 11/312,279, report issued Jun. 24, 2008, pp. 1-8.

"PCT International Search Report and Written Opinion from International Application No. PCT/US2006/047215", corresponding to U.S. Appl. No. 11/312,279, mailed Jun. 19, 2007, pp. 1-17.

Kerr, Martha, "Shock Rate Cut 70% with ICDs Programmed to First Deliver Antitachycardia Pacing: Results of the PainFREE Rx II Trial. NewsRhythms", NewsRhythms. MesScape CRM News 2003. www.medscape.com.

Wathen, et al., "Shock Reduction Using Antitachycardia Pacing for Spontaneous Rapid Ventricular Tachycardia in Patients With Coronary Artery Disease", Circulation, 104:796-801 (2001).

\* cited by examiner

METHODS AND SYSTEMS FOR CHARACTERIZING CARDIAC SIGNAL MORPHOLOGY USING K-FIT ANALYSIS

This application claims the benefit of U.S. Provisional Application No. 61/245,871, filed Sep. 25, 2009, the content of which is herein incorporated by reference.

TECHNICAL FIELD

This disclosure relates generally to systems and methods for analyzing data from a medical device, and, more particularly, to medical systems and methods that can be used to analyze cardiac signal data.

SUMMARY OF THE INVENTION

Embodiments of the invention are related to medical systems and methods that can be used to analyze and collect information from implanted medical devices, amongst other things.

In one embodiment, a method for automatically analyzing a cardiac signal includes the step of providing an episode database on a computer storage medium including a plurality of episode data records of one or more patients. Each episode data record includes a cardiac signal from at least one data-generating device. The method also includes the step of selecting one or more of the N beats to be one or more beat templates, for at least a first cardiac signal having N beats. Another step is determining a value K for the cardiac signal using a computer system where K beat templates can represent all the N beats in the cardiac signal.

In another embodiment, a method for automatically analyzing a cardiac signal includes the step of providing an episode database on a computer system including at least one episode data record. Like the first embodiment, each episode data record includes a cardiac signal from at least one data-generating device and the cardiac signal has N beats. Another step is selecting a range of possible values for K. For each set s of K beats, a series of steps are performed that will be referred to as a first loop. Within the first loop is a nested, second loop, where for each beat b not in the set s, the processor finds the beat s(b) in s that is closest to b and calculates a morphology distance between s(b) and b. The next step of the nested, second loop is for each beat b, calculating a morphology distance compilation value for each set S, wherein the morphology distances are used in calculating the morphology distance compilation value. Once the second, nested loop has been performed for each beat b not in the set s, then the next steps of the first loop are comparing the morphology distance compilation values to identify which set S of K beats results in the best representation of the cardiac signal based on the morphology distance compilation value, and recording the morphology distance compilation value and recording set S of K beats. Based on the morphology distance compilation values for each value of K, a best value of K for the EGM is determined, where K beat templates can represent all the beats in the EGM signal.

In one embodiment, for a particular cardiac signal, K beat templates are presented to a user on a display device to represent the signal morphology of the particular cardiac signal. In one embodiment, for a particular cardiac signal, M beat templates are presented to a user on a display device to represent the signal morphology of the particular EGM, where M is less than K.

In yet another embodiment, a system automatically analyzes a cardiac signal and includes an episode database including a plurality of episode data records of one or more patients, wherein each episode data record includes a cardiac signal from at least one data-generating device. The system further includes an adjudication processor configured to perform the following steps: for at least a first cardiac signal having N beats, selecting one or more of the N beats to be one or more beat templates; and determining a value K for the cardiac signal where K beat templates can represent all the N beats in the cardiac signal.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

Figure 1:
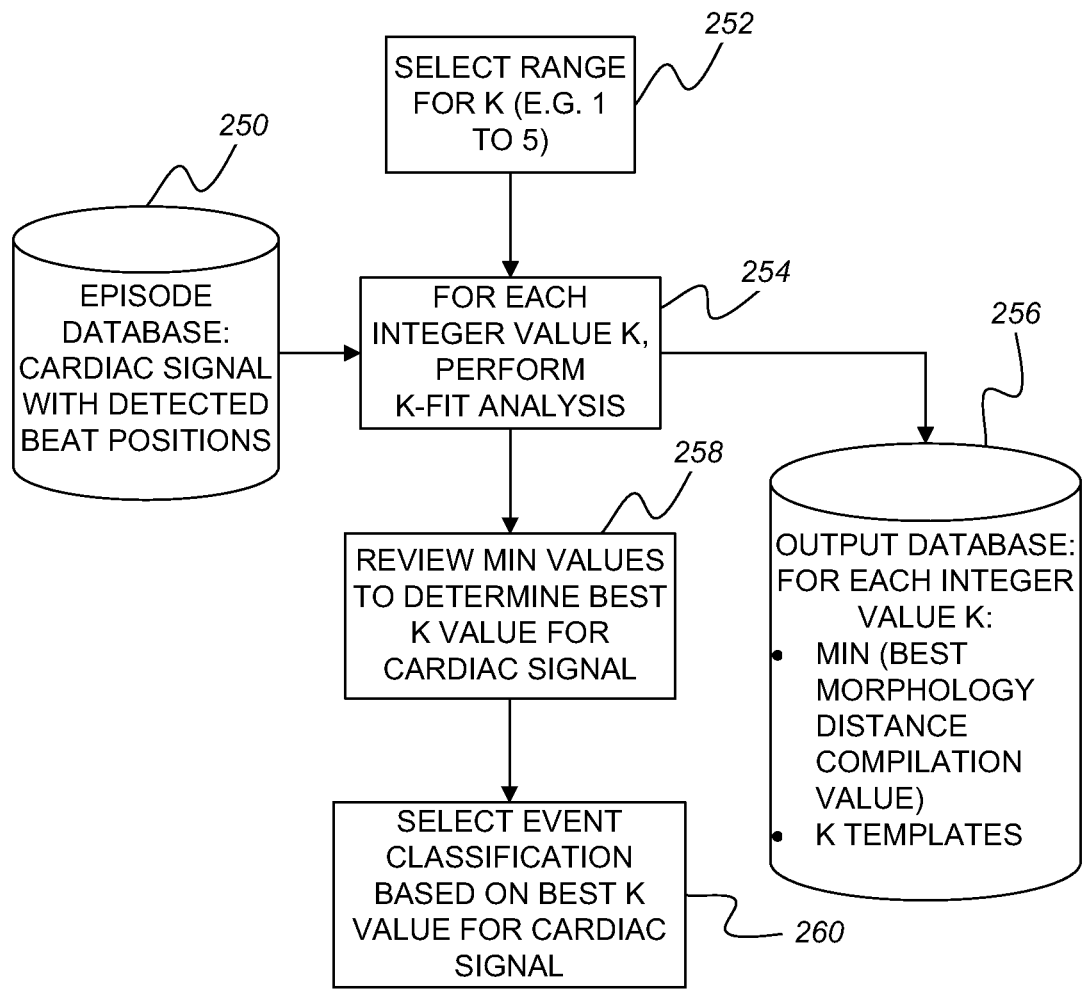
FIG. 1 is a flowchart illustrating the steps of one embodiment of a method of automated analysis of signal morphology of a cardiac signal.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

This disclosure relates generally to medical data-generating devices and, more particularly, to systems and methods for analyzing information from such medical devices. In particular, this disclosure relates to systems and methods for automatically determining signal morphology information from cardiac signals. Examples of cardiac signals are electrograms (EGMs), heart sound signals, impedance signals, and pressure signals. In some embodiments, the data-generating devices are implanted, while in some embodiments, the data generating devices are external or subcutaneous. In some embodiments, the information gathered includes an intracardiac EGM.

Such data-gathering devices may be a part of a cardiac rhythm management system (CRM systems) that includes an implantable cardiac rhythm management device (CRM device), an external interface device and a patient management computer system. An implanted cardiac rhythm management (CRM) device can be used to provide pacing therapy to a patient with sinus node dysfunction, in one example, where the heart fails to properly initiate depolarization waves, or an atrio-ventricular conduction disturbance, where the conduction of depolarization waves through the heart tissue is impaired, or to support and treat patients with many different types of cardiac issues.

A cardiac signal is a record of the heart's activity. An electrogram (EGM) is a recording of cardiac electrical activity. The science of morphology deals with interpretation of the shape characteristics of the cardiac signals, such as EGM signals, where such shape characteristics include amplitude, width and contour. The morphology of a cardiac waveform can be used to discriminate between different types of cardiac arrhythmias and other cardiac events, and morphology information can be very useful to clinicians treating the patient.

A few specific types of cardiac arrhythmias will now be discussed, along with the morphology characteristics that are observed in a cardiac signal during these types of arrhythmias. In addition to referring to the science of the study of cardiac signals, the term "morphology" will be used to refer to the amplitude, width and contour of a particular portion of a cardiac signal, such as a beat-to-beat portion of an EGM.

Cardiac arrhythmias that originate above the ventricle of the heart are referred to as supraventricular arrhythmias. Two examples of such arrhythmias are atrial fibrillation (AF) and atrial flutter, which both involve rapid uncoordinated contractions of the atria, resulting in inefficient atrial pumping action. It has been observed that a ventricular EGM during supraventricular arrhythmias includes typically just one type of morphology, since the ventricular activities are still a result of atrial activities conducted from the AV node. A morphology template constructed from one of the beats within the ventricular EGM would therefore be very similar to the remainder of the beats in the ventricular EGM.

Cardiac tachy arrhythmias originating in a ventricle are called ventricular tachyarrhythmias (VT). Ventricular tachyarrhythmias involve rapid ventricular contractions and can degenerate into ventricular fibrillation (VF), which produces extremely rapid non-coordinated contractions of the ventricles. Ventricular fibrillation is fatal unless the heart is returned to a normal sinus rhythm within a few minutes. The morphology of a patient cardiac signal is one way to determine whether the patient is experiencing monomorphic ventricular tachyarrhythmia, polymorphic ventricular tachyarrhythmia or ventricular fibrillation. In a ventricular EGM of a patient experiencing monomorphic ventricular tachyarrhythmia, only one or two morphologies are typically present. In a ventricular EGM of a patient experiencing ventricular fibrillation or polymorphic ventricular tachycardia (PVT), multiple morphologies are often observed, such as three or more different morphologies.

Each of these different types of cardiac arrhythmias warrants a different response from an implanted cardiac device. For example, a monomorphic ventricular tachyarrhythmia is typically terminable with pacing of the heart, while a polymorphic ventricular tachyarrhythmia or ventricular fibrillation is typically not terminable with pacing of the heart. The morphology of a cardiac signal such as an EGM waveform can be processed in an automated manner to determine the proper arrhythmia characterization that the patient has experienced. It is also useful for an automated system to identify a representative morphology portion of the cardiac signal, such as in order to save it in the medical record of the patient or to present to a clinician working with the patient.

It is also helpful for an automated system to be capable of determining when the morphology of a patient's cardiac signal has changed, such as to verify that different type rhythms have occurred. Sometimes the difference between two different morphologies is subtle, and current techniques for automatically determining morphology and extracting morphology are not always successful.

K-Fit Analysis

As a result, a signal morphology analysis system, K-Fit analysis, has been developed that determines the signal morphology variability of a cardiac signal to determine how many different templates are needed to provide quality fits for all or a subset of segments of the cardiac signal portion that is being analyzed. The letter K will be used to indicate the number of templates in the discussion herein. The system is also capable of identifying a portion of the cardiac signal that is representative of one of the morphologies present in the cardiac signal, for example, in order to save it in the medical record of the patient or to present to a clinician working with the patient.

K-fit analysis is a mathematical method which is used to divide n data points into K groups of data. The starting point for K-Fit analysis is a set of observations $(x_1, x_2, x_3, x_4, \ldots x_n)$. For example, a set of cardiac beat morphologies from a cardiac signal is a set of observations that can be input for a K-fit analysis.

The analysis seeks to find K observations (templates) that can result in the best match with the complete set of observations. An adjudication processor uses the K-fit analysis to determine the signal morphology complexity or variability. Templates are constructed from the original data in the cardiac signal. Then a determination is made how well a signal can be represented by different numbers of templates ranging from 1 to K templates, where the high end of the range for K is a value selected by the user of the system.

FIG. 1 is a flow chart illustrating the steps of one embodiment of a method for automated analysis of the signal morphology of a cardiac signal. An episode database 250 provides a cardiac signal with detected beat positions which is an input for the method steps. The beat positions may be detected by many different methods. For example, many data-generating devices provide indications of beat positions along with the cardiac signal. Another method is to define and identify the beats as being a portion of the cardiac signal between one sensed peak and a previous sensed peak, between one sensed minimum and a previous sensed minimum, or between sensed periods of no activity.

An initial step 252 is for a user to determine the high end of the range of possible values for K. It is also possible for this step to be a default setting in the system. For example, K could always be set to be 3, 4, 5, 6 or another integer. Once the maximum value for K is set, then, for each whole number value starting with one and continuing until the maximum value of K, a K-fit analysis is performed at step 254. For each value of K, the system outputs a morphology distance compilation value. The morphology distance compilation value, also referred to herein as "Min" is a representation of how well a particular template or set of templates can represent all of the beats or a subset of all the beats in the cardiac signal, as will be described in more detail herein. In addition to outputting a morphology distance compilation value (Min), the morphologies of the K templates are output for each value of K to the output database 256.

Next, the morphology distance compilation values for each K are reviewed, in order to determine the best K value for the cardiac signal. In many embodiments, the lower the value of Min, the better the fit between the K templates and the K subsets of the cardiac signal. But if the value of Min decreases only slightly as the value of K increases by one, e.g. smaller than a preset percentage, then the lower value for K is likely the best fit.

Figure 2:
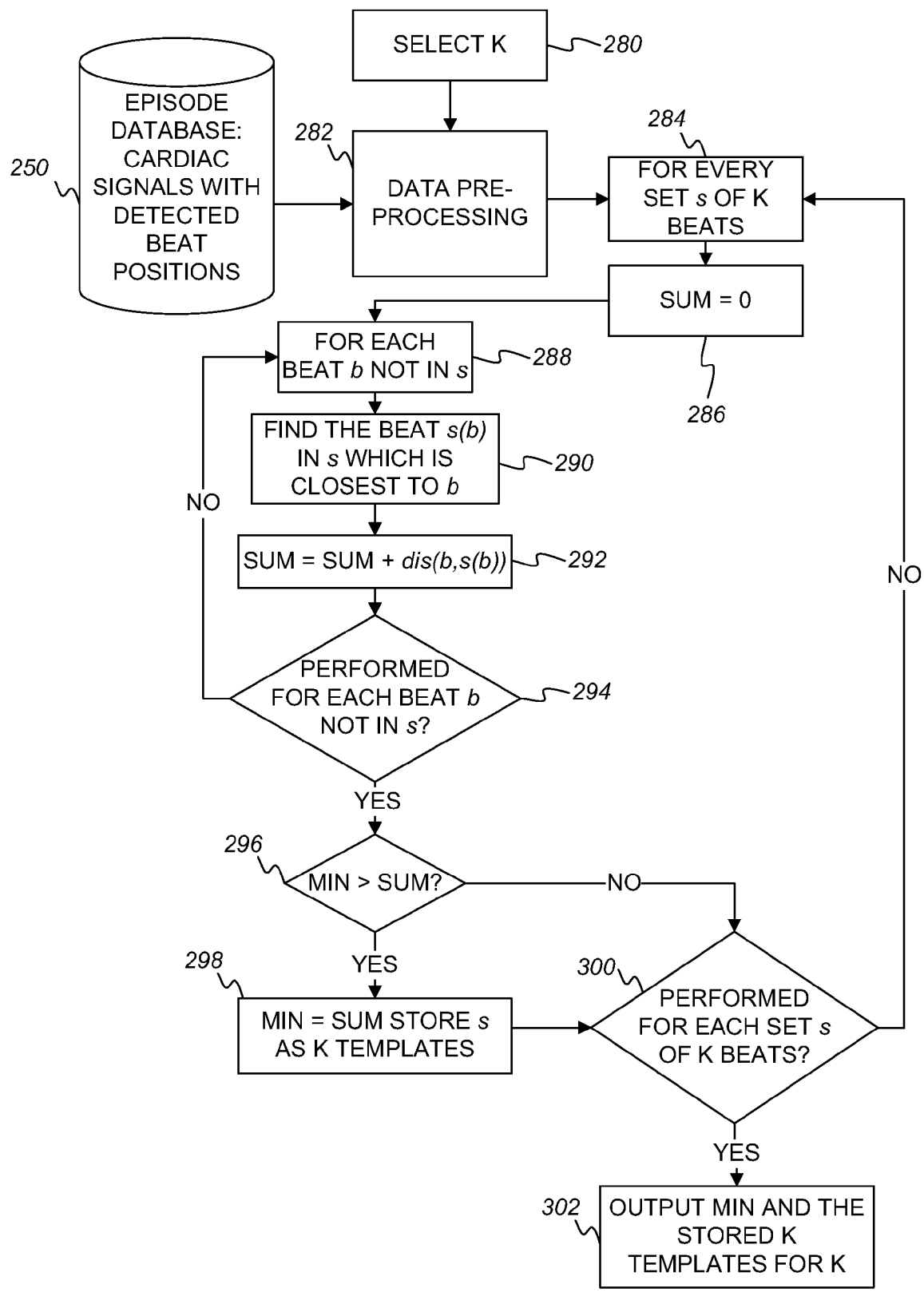
FIG. 2 is a flowchart illustrating the steps of K-fit analysis of one embodiment of a method of automated analysis of a cardiac signal.

FIG. 2 illustrates one example of how Min (the best value for the morphology distance compilation value) is determined for each value of K. This example involves calculating a morphology distance sum for each beat template, where the morphology distance sum is the sum of all the morphology distances between a particular beat template and the rest of the members of the signal or signal subset. Then, the smallest morphology distance sum is identified, which is also referred to as the minimum morphology distance sum. For this example, the best morphology distance compilation value is the minimum morphology distance sum. However, other functions besides summation can also be used. For example, multiplication of the morphology distances or another function could be used to calculate a morphology distance compilation value.

At 250 in FIG. 2, the episode database provides cardiac signals with detected beat positions as the input for the analysis. The value for K for the particular phase of the analysis is determined in step 280. Data pre-processing may be performed, for example, each beat in the cardiac signal can be normalized to be the same width in step 282. Some data-generating devices output normalized cardiac signals, and so that this step would not be necessary. Also, as a preliminary step in one embodiment, the Min value is set to infinity.

Now referring to step 284, for each set s of K beats, a series of steps 286-300 that will be referred to as a first loop is performed as described below. For example, if K is two for a particular phase of the analysis, then set S includes all possible combinations s of two beats in the signal. The steps of the first loop described herein are performed for each set s of two beats within the cardiac signal. The beats in each set s do not need to be consecutive beats. The term Sum is set to zero at step 286. Step 288 is the first step in a nested, second loop 288-294, where for each beat b not in the set s, the processor finds the beat s(b) in s that is closest to b in step 290. This determination is made using one of many techniques available to quantify the morphology difference or distance between a first beat and a second beat. Examples of different distance measures include Euclidean distance, Mahalanobis distance and Manhattan distance.

Once the beat s(b) has been identified that is the closest beat in the set s to beat b, then the value for the term Sum is overwritten to be the previous value for Sum plus the distance between s(b) and b at step 292:

$$\text{Sum} = \text{Sum} + dis(b, s(b))$$

As mentioned previously, the morphology distance sum is described herein as an example of a morphology distance compilation value. Instead of a morphology distance sum for a particular beat template, a function different than summation, such as multiplication, may be used to compile the morphology distances into a morphology distance compilation value that can be compared to others.

At step 294, the system determines if the nested second loop has been performed for each beat b not in s. If no, the system returns to step 288 and performs the nested loop for the next beat b in the cardiac signal that is not in the set s. After the nested loop has been performed for each beat b not in the set s, the system continues to step 296, where the value for Sum is compared to the value for Min. If Min is larger than Sum, then Min takes on the value of Sum. Min will always be larger than Sum for the first iteration of values because Min was initially set at infinity. If Min is not larger than Sum at step 296, then the system determines if the analysis has been performed for each set s of K beats at step 300. If not, the system returns to step 284 and restarts the first loop of steps with the next set s of K beats.

After each set s of K beats is analyzed, the value of Min is replaced by a new lower value for Min at step 298 if a set is identified that is a better fit for the cardiac signal, and the set s is stored as the K templates for the particular value of K that was selected at step 280.

The distance sum may also be normalized based on the number of observations, e.g. sum=sum/(number of observations−K), so that the sum from different K values may be compared.

For example, for K=1, each set s would have only one member. The analysis would output a beat template selected from one of the beats in the cardiac signal, and a Min value which would indicate how well the beat template fit the entire cardiac signal. For K=2, set S includes all possible combinations s of two beats from a signal. The analysis would output the two beat templates s that produced the best morphology distance compilation value, or minimum morphology distance sum or Min, and would output the value Min for K=2, which would indicate how well the two beat templates fit the cardiac signal. The analysis would then be performed for K=3. In this case, set S includes all possible combinations s of three beats from the signal. The analysis would output three beat templates and a value for Min.

Rules for Determining the Appropriate Value of K for K-Fit Analysis for a Particular Cardiac Signal Based on the output values of the morphology distance compilation value, or minimum morphology distance sum, for each value of K, a user can determine how many templates are needed to represent the cardiac signal, which is called the K-fit value for a particular cardiac signal. The K-fit value in turn can be used to make a characterization of the cardiac signal such as an arrhythmia characterization. It is also possible for the processor to automatically determine the K-fit value. The lower the value of the minimum morphology distance sum (Min), the better the fit between the K templates and the cardiac signal. But if the value of Min decreases only slightly as the value of K increases by one, either by less than a pre-set percentage, e.g. 15%, or by less than a pre-set absolute difference, e.g. 0.005, then the lower value for K is likely the best fit. A preset threshold may also be used to facilitate the selection of K. The smallest K that results in a distance smaller than a pre-set threshold, e.g. 0.02, may be used.

Figure 3A:
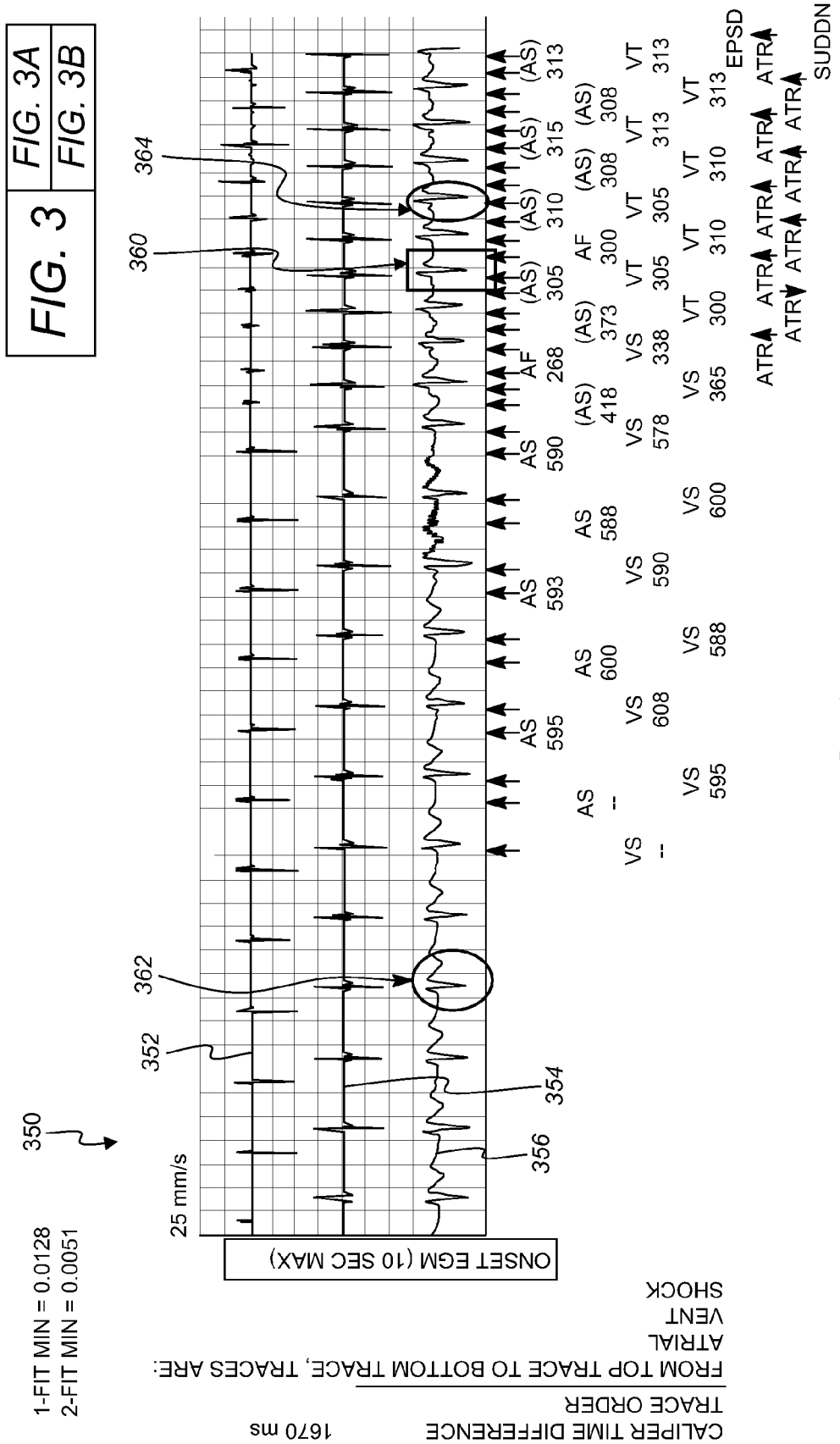
FIG. 3 is an EGM from a patient experiencing a supraventricular tachyarrhythmia (SVT) episode, with beat template candidates indicated on the EGM for different K-fit analysis outputs, partitioned into FIG. 3A and FIG. 3B.
Figure 3B:
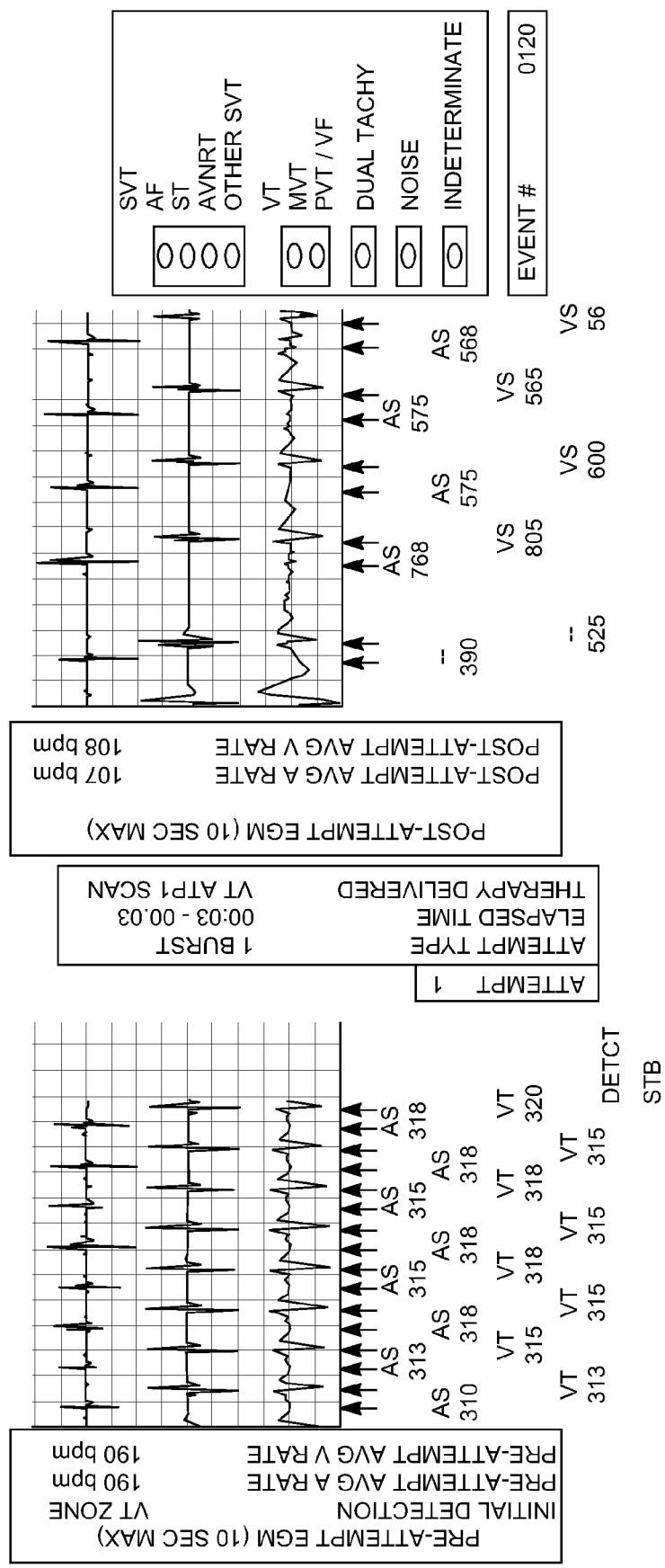

FIG. 3 shows an example of a cardiac signal in the form of an EGM 350 for a patient experiencing a supraventricular tachycardia (SVT) arrhythmia episode. The EGM 350 includes three channels: an atrial sensing channel 352, a ventricle sensing channel 354 and a shock channel sensing 356. The EGM 350 was input into the K-fit analysis described above, using a Euclidean distance measure to analyze the shock channel of the EGM 350. In the following examples, a pre-set distance threshold of 0.02 is used to select K. The smallest K that results in a distance less than 0.02 is used to represent the cardiac signal.

For K=1, the Min value was 0.0128 and the beat template 360 was output. For K=2, the Min value was 0.0051 and the two beat templates 362 and 364 were output. Since the Min value for K=1 is already less than the pre-set threshold of 0.02, the K-fit analysis concluded that K=1 is the appropriate outcome for the K-fit analysis, and that beat template 360 is an appropriate beat template to represent the EGM 350. The K-fit analysis further correctly concluded that the patient was experiencing an SVT episode.

Figure 4A:
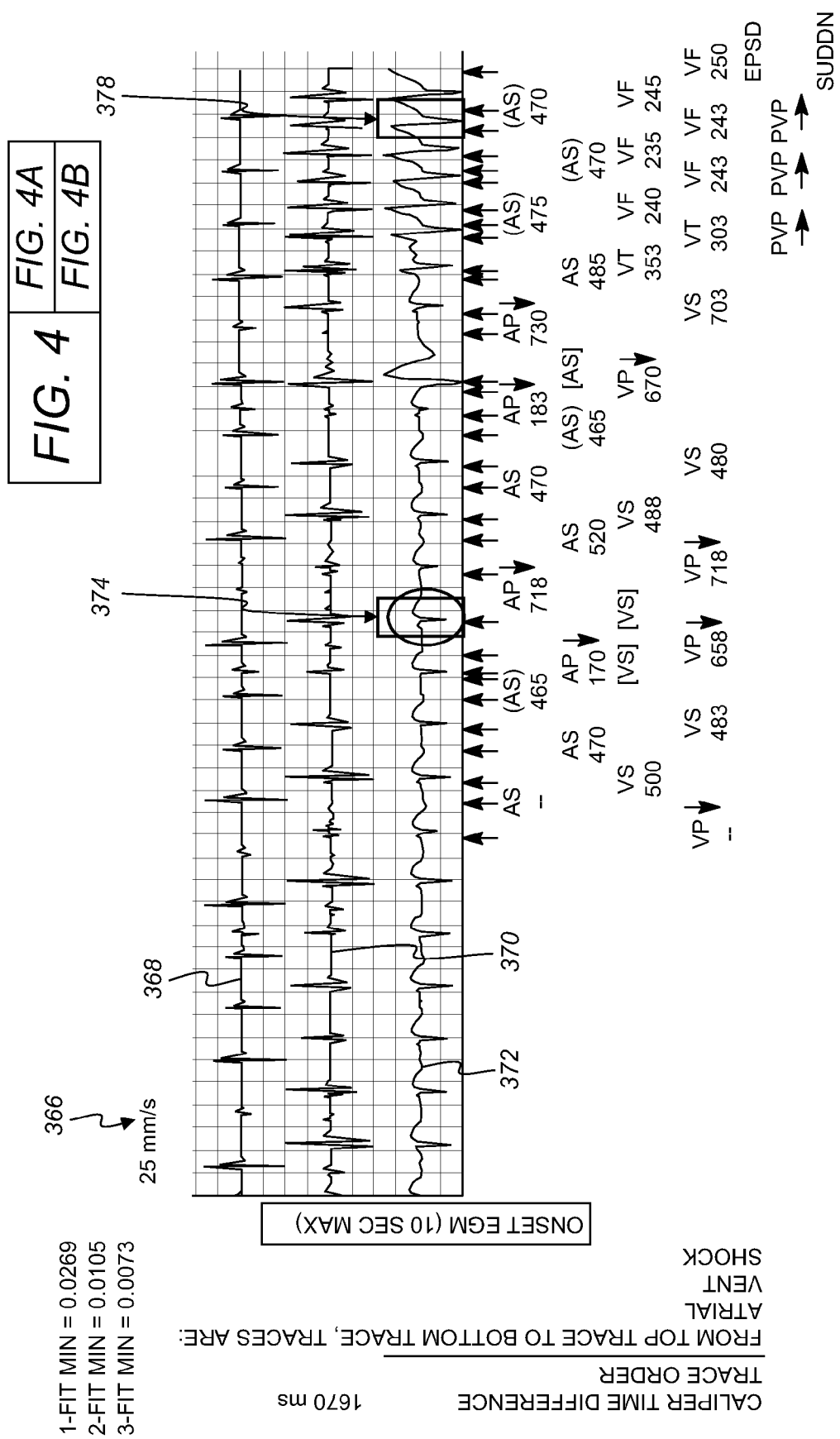
FIG. 4 is an EGM from a patient experiencing a monomorphic ventricular tachyarrhythmia episode (MVT), with beat template candidates indicated on the EGM for different K-fit analysis outputs, partitioned into FIG. 4A and FIG. 4B.
Figure 4B:
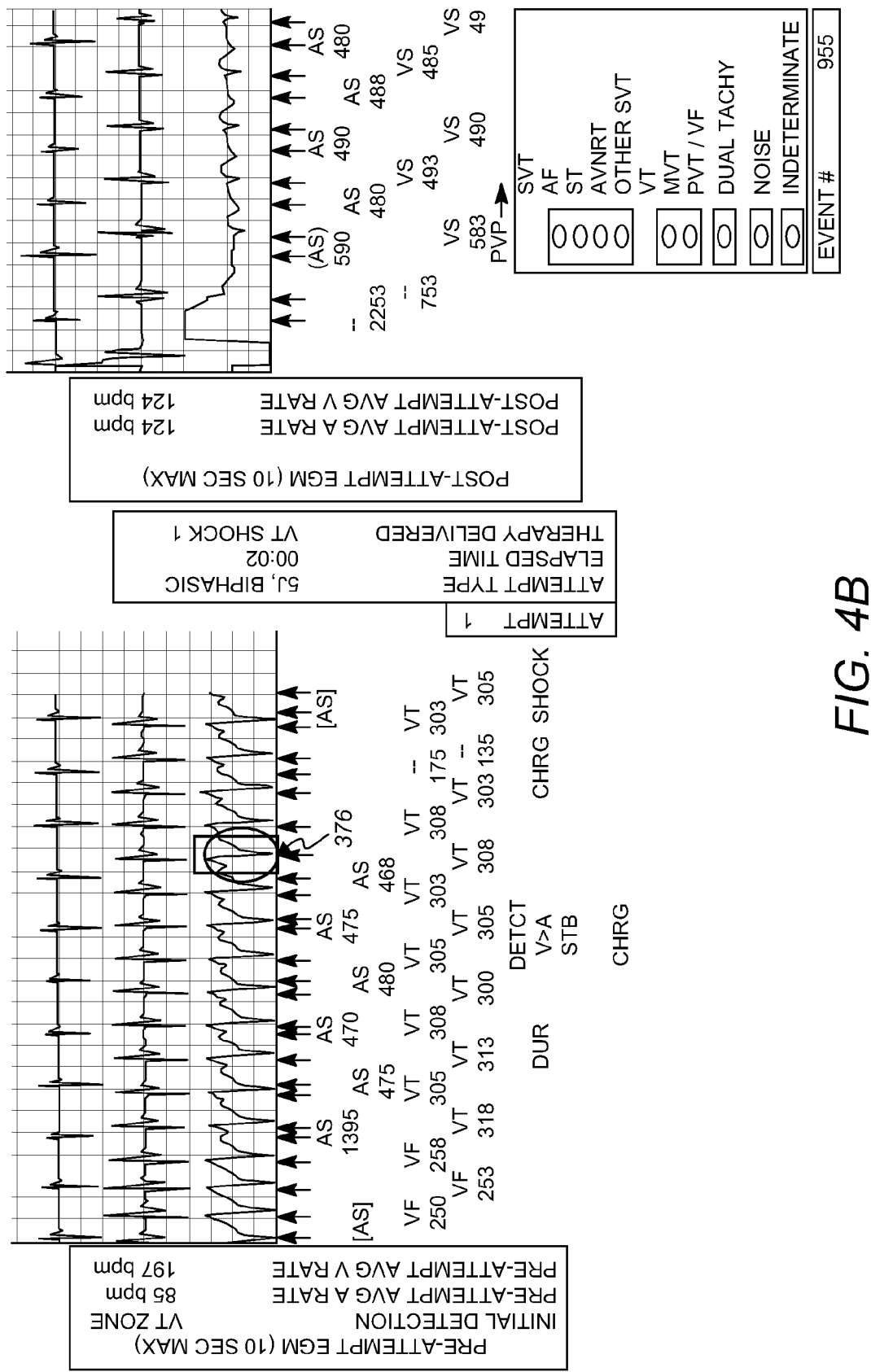

FIG. 4 shows another example of a cardiac signal in the form of an EGM 366, but for a patient experiencing a monomorphic ventricular tachyarrhythmia (MVT) episode. The EGM 366 includes three channels: an atrial sensing channel 368, a ventricle sensing channel 370 and a shock channel sensing 372. The EGM 366 was input into the K-fit analysis described above, using a Euclidean distance measure to analyze the shock channel of the EGM 366.

For K=1, the Min value was 0.0269. For K=2, the Min value was 0.0105 and the two beat templates 374 and 376 shown in ovals were output. For K=3, the Min value was 0.0073 and the three beat templates 374, 376 and 378 shown in boxes were output. Since the Min value for K=2 is already less than the pre-set threshold of 0.02, and considerably smaller than the Min value for K=1, and since the Min value for K=3 only decreased slightly (absolute difference is 0.0032) as K increased from 2 to 3, the K-fit analysis concluded that K=2 is the appropriate outcome for the K-fit analysis, and that beat templates 374 and 376 are appropriate beat templates to represent the EGM 366. The K-fit analysis further correctly concluded that the patient was experiencing a normal sinus rhythm that changed to an MVT episode.

Figure 5A:
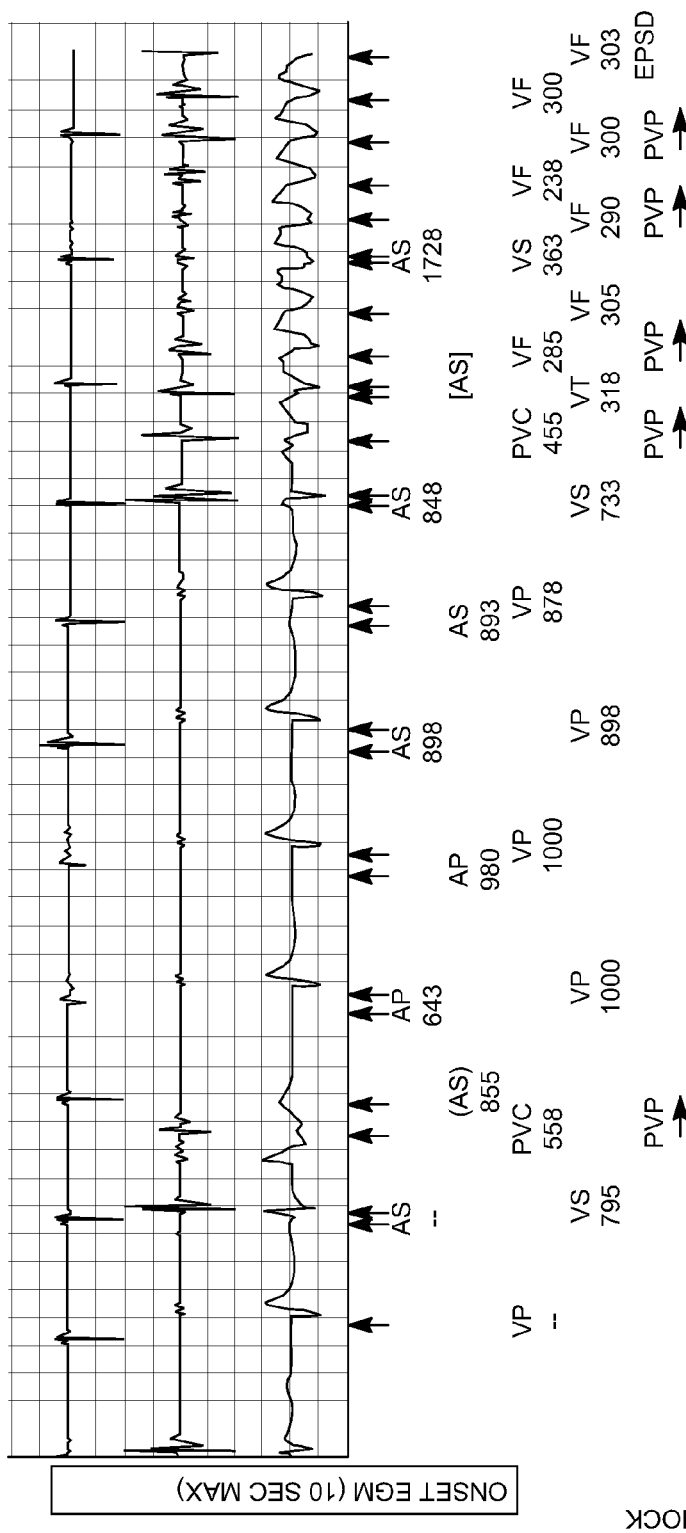
FIG. 5 is an EGM from a patient experiencing a polymorphic ventricular tachyarrhythmia episode (PVT), with beat template candidates indicated on the EGM for different K-fit analysis outputs, partitioned into FIG. 5A and FIG. 5B.
Figure 5B:
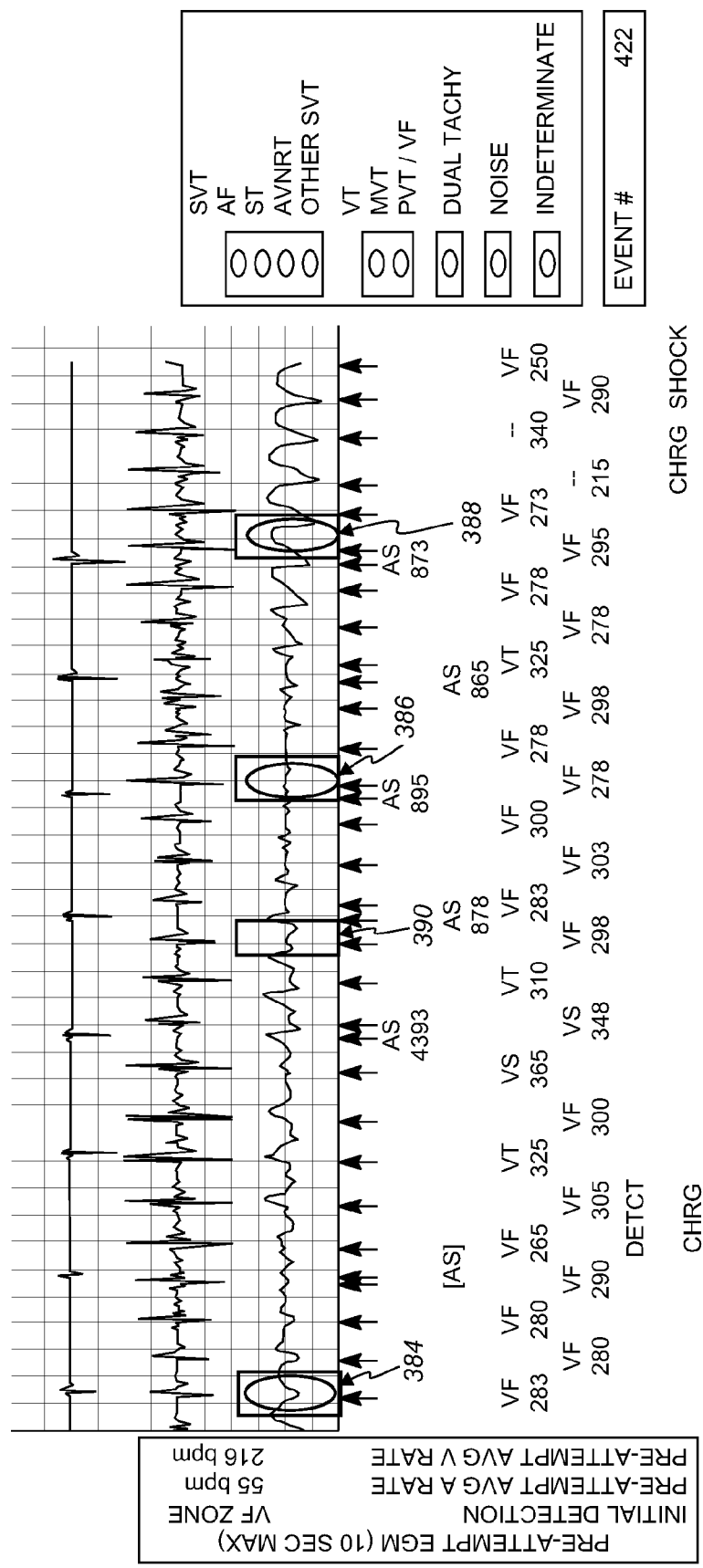

FIG. 5 shows another example of a cardiac signal in the form of an EGM 382, but for a patient experiencing a polymorphic ventricular tachyarrhythmia (PVT) arrhythmia episode. The EGM 382 includes three channels as in FIGS. 3 and 4. The EGM 382 was input into the K-fit analysis described above, using a Euclidean distance measure to analyze the shock channel of the EGM 382.

For K=1, the Min value was 0.0426 and for K=2, the Min value was 0.037. For K=3, the Min value was 0.0346 and the three beat templates 384, 386 and 388 shown in ovals were output. For K=4, the Min value was 0.0330 and the four beat templates 384, 386, 388 and 390 shown in rectangles were output. Since the Min values for K=3 and K=4 are larger than the pre-set threshold of 0.02, it is clear that even four templates is not sufficient to accurately describe the cardiac signal. As a result, the K-fit analysis correctly concluded that the patient was experiencing a PVT episode.

Rules for Episode Characterization Based on Output of K-Fit Analysis and Other Factors The K-fit analysis results can be used to automatically characterize an episode. For example, an arrhythmia characterization can be automatically assigned to the cardiac signals in some embodiments. In other embodiments, human reviewers will look at the template and K value and then characterize the episode. In other embodiments, characterization data about the episode is automatically generated, but those characterizations can be reviewed and overwritten by human reviewers. Some examples of an arrhythmia characterization include monomorphic ventricular tachycardia (MVT), polymorphic ventricular tachycardia/ventricular fibrillation (PVT/VF), atrial fibrillation (AF) and other supraventricular tachycardia (SVT). Many other types of arrhythmia characterization are possible, as will be further described herein.

In addition, many other types of episode characterization are possible in various embodiments, such as ST elevation analysis to detect ischemia.

The chart below shows the arrhythmia characterizations that will be assigned based on the best K-fit value for a particular cardiac signal in one embodiment.

| K-fit Value | Arrhythmia Characterization |
|---|---|
| 1 | SVT |
| 2 | MVT |
| 3 or more | PVT/VF |

For PVT/VF, it is usually necessary to use more than 4 beats to represent the cardiac signal. For MVT, two beats are typically needed: one template for normal sinus beats and the other for tachy beats. For AF or other SVT, only one beat is needed to describe the cardiac signal.

In addition to using the number of K to classify episodes, the distances, best morphology compilation value, or minimum morphology distance sum at different K may also be used to classify the episodes. For example, each episode may be represented by a feature vector consisting of the distances at different K, e.g. [Min at K=1, Min at K=2, Min at K=3, Min at K=4], then a pattern recognition algorithm, such as decision tree, or support vector machines, may be used to provide the episode classifications.

In addition to the K-fit value, other information about the cardiac signal may be considered when making the arrhythmia characterization. For example, the system may consider whether the ventricular rate is faster than the atrial rate, which would indicate a ventricular tachycardia. The system may also consider how the tachycardia was initiated by examining the different channels of the EGM to see which channel was the location of the first fast beat. For example, if the first fast beat is located in the atrial channel, then it is likely this episode is a supra-ventricular beat. This additional information, along with the K fit analysis results, may be used to enhance the classification performance.

Further Examples of Characterization Data

Some examples of characterization data, specifically arrhythmia characterizations, have already been mentioned, such as MVT, PVT/VF, SVT and AF. Other examples of arrhythmia characterizations are atrial-ventricular (AV) nodal re-entrant tachycardia (AVNRT), atrial flutter (AFL), atrial tachy (AT), sinus tachy (ST), dual tachy (DT), pacemaker-mediated tachycardia (PMT), one-to-one AV conduction with constant ventricular morphology, oversensing, noise and indeterminate. It is also possible for the system to provide more or fewer arrhythmia characterizations than those listed. In one embodiment, the arrhythmia characterization options include at least polymorphic ventricular tachycardia/ventricular fibrillation (PVT/VF), monomorphic ventricular tachycardia (MVT) and supraventricular tachycardia (SVT). In another embodiment, the arrhythmia characterization options include at least polymorphic ventricular tachycardia/ventricular fibrillation (PVT/VF), monomorphic ventricular tachycardia (MVT), atrial fibrillation (AF) and other supraventricular tachycardia (SVT). In various embodiments, there are three or more, four or more, five or more and six or more options for the arrhythmia characterization.

Examples of Distance from K-Fit

Figure 6:
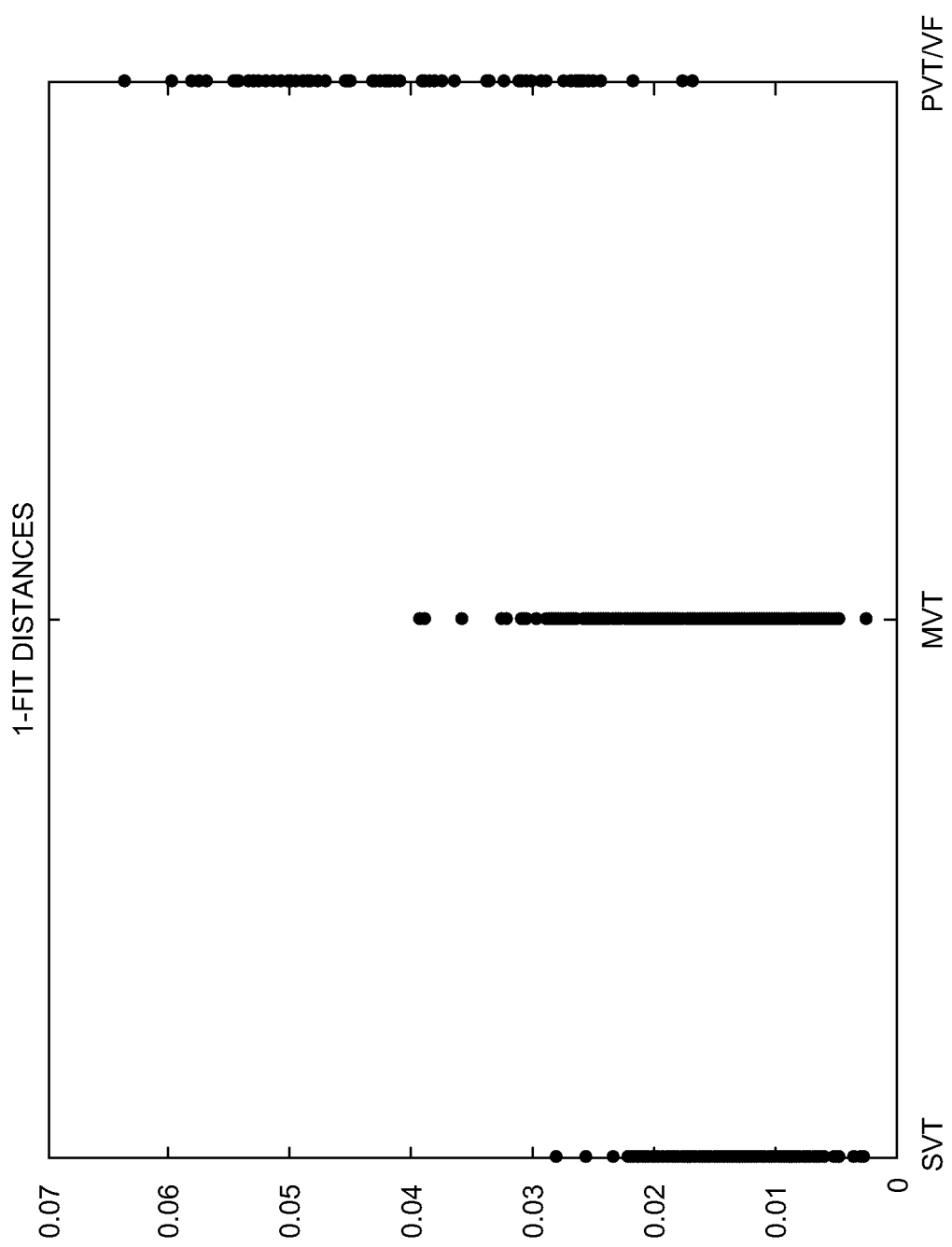
FIGS. 6-9 are graphs plotting the K-fit analysis output values for a minimum morphology distance sum on the vertical axis against the arrhythmia characterization type on the horizontal axis.
Figure 7:
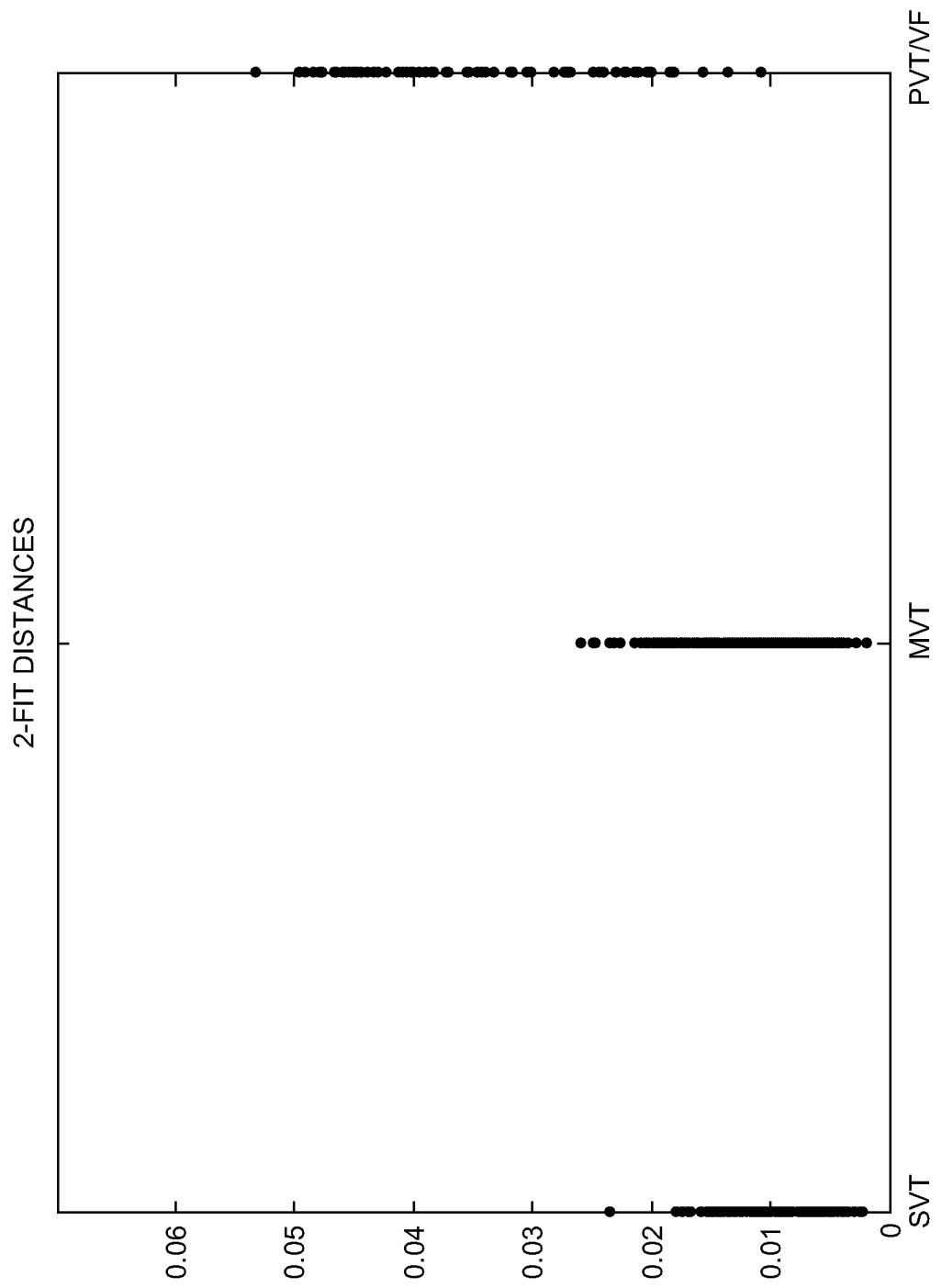
Figure 8:
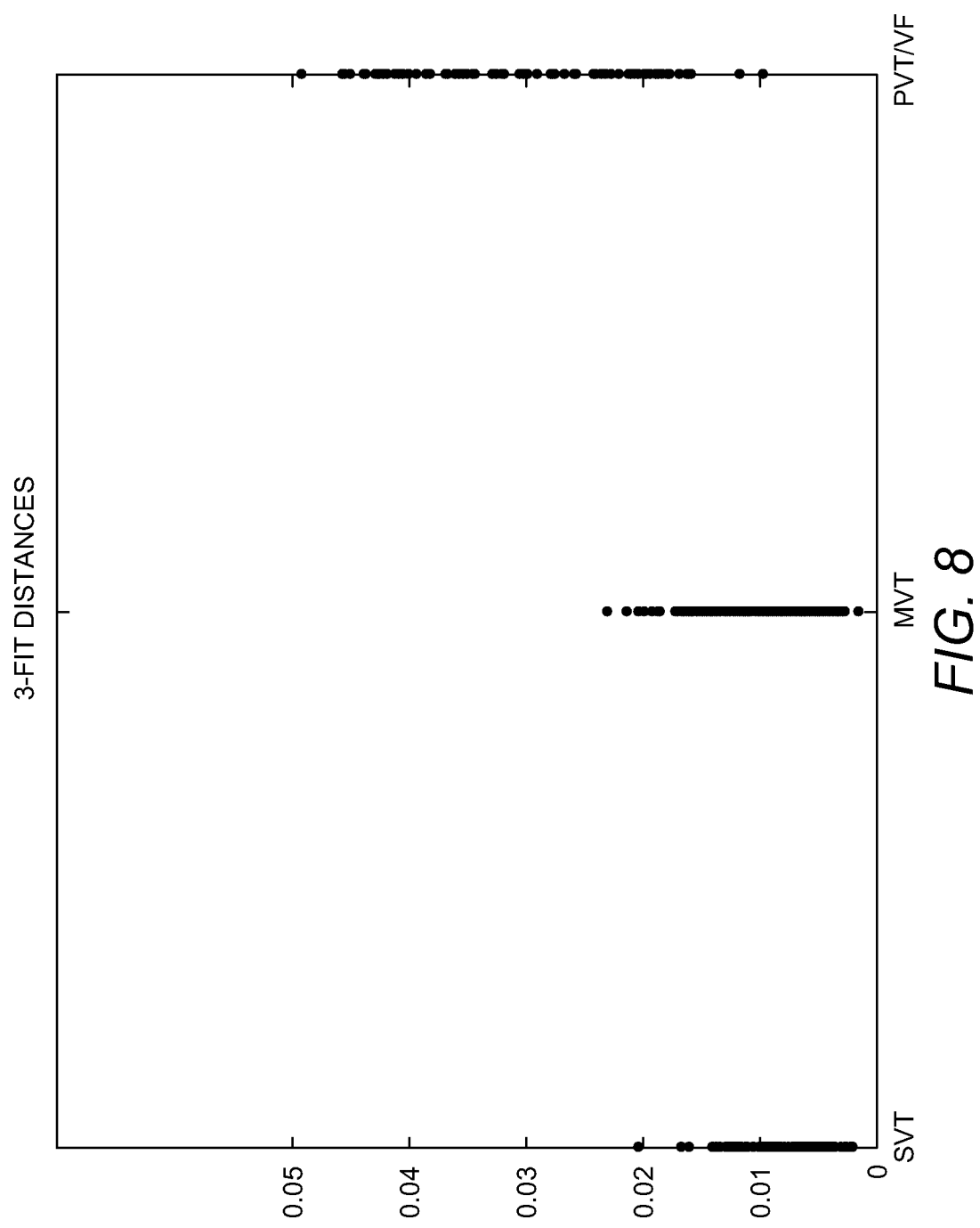
Figure 9:
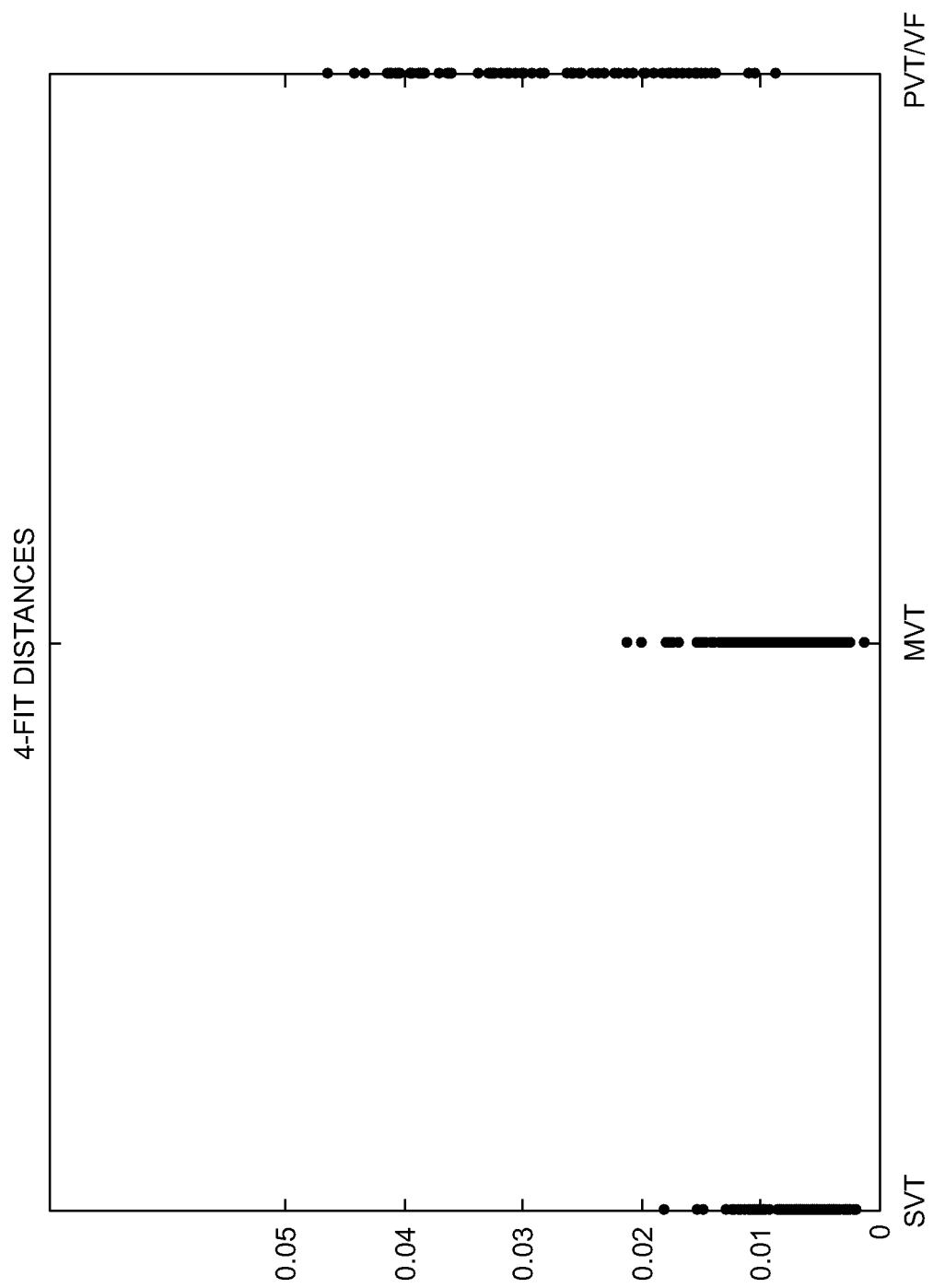

The K-fit analysis described herein was tested using a database of cardiac signals with known arrhythmia characterizations as determined by human reviewers. FIGS. 6, 7, 8 and 9 are graphs plotting the K-fit analysis output value for minimum morphology distance (Min) on the vertical axis against the arrhythmia characterization type as determined by the human reviewer on the horizontal axis. FIG. 6 shows the Min values for dozens of cardiac signals that were analyzed using K=1. FIG. 7 shows the Min values for the same cardiac signals that were analyzed using K=2, while FIG. 8 shows the outputs for K=3 and FIG. 9 shows the outputs for K=4.

For all four of FIGS. 6-9, the SVT column appears to be very similar and the Min values are small, about 0.02 and less. Because SVT episodes are characterized by relatively consistent beat to beat morphologies, the Min values do not decrease very much as the K value increases. For these episodes, K=1 is the best fit. With only one beat template, it is possible to represent the entire cardiac signal with good performance.

For the MVT column, there is a decrease in the Min values for K=2 compared to K=1. There is less of a decrease in the Min values as for K=3 compared to K=2, indicating that K=2 is the best fit for these episodes. The Min values are less than 0.02 in most cases for K=2, 3 and 4, indicating that these are fairly simple cardiac signals.

For the PVT columns on FIGS. 6-9, the Min values are significantly larger than 0.02 for all of the K values in most cases, indicating that these are fairly complex signals. The Min values do not change very much whether K is 1, 2, 3 or 4.

Other Applications of K-Fit Analysis

K-Fit analysis can be used in any application which requires template generation. For example, automatic capture verification, in which the template for a captured beat is necessary to establish the capture verification parameters, is a candidate for K-Fit analysis. Another candidate is rhythm identification, in which a template is established for a normal sinus beat. K-Fit analysis can also be applied to ischemia detection through monitoring S-T segment elevation.

In addition to using electrical signal as an input, K-Fit analysis may also be applied to signals from other physiological sensors, such as pressure sensors, impedance sensors, and heart sound sensors, for different applications, such as arrhythmia detection. Published U.S. Application 2009-0131996 A1, titled "Tachycardia hemodynamics detection based on cardiac mechanical sensor signal regularity" describes how mechanical sensor signals can be used to detect tachycardia hemodynamics, and is hereby incorporated herein by reference in its entirety.

The K-Fit analysis may also be use to trend the long term morphology changes of a physiological signal. In one embodiment, a pre-set distance threshold may be used. A 1-Fit template may be obtained from a segment of signals. If the Min from the 1-Fit analysis is not greater than the pre-set threshold, the 1-Fit template can be used to represent this segment of signals. Otherwise, the length of the segment is reduced until the 1-Fit analysis is less than the pre-set threshold.

K-Fit Analysis Using Complex Beat

It is possible to perform the K-fit analysis using a comparison of complex beats of the cardiac signals. A complex beat is defined as a combination of the morphologies in all channels, for example, an atrial channel, a ventricle channel and a shock channel and the length of the beat interval. The beat interval can be determined in many different ways, such as by the interval between two adjacent sensed peaks in ventricular channel. When calculating the difference between two complex beats cb2 and cb1, the distances in all three channels will all be counted, as well as the differences between the interval lengths. One possible embodiment is described as:

$$dis(cb1,cb2)=w_a dis_{atrial}(cb1,cb2)+w_v dis_{ventricular}(cb1,cb2)+w_s dis_{shock}(cb1,cb2)+w_l |length(cb1)-length(cb2)|.$$

The terms $w_a$, $w_v$, $w_s$ and $w_l$ are weights, which are equal in one embodiment.

Identifying a Transition Beat for an MVT Episode

As discussed previously, a typical MVT episode includes normal sinus rhythm beats and tachy beats. It can be valuable to identify the transition beat between the normal and tachy beats, and a K-fit analysis can be used to identify the transition beat, as well as templates for the normal and tachy beats before and after the transition.

A method has been developed to identify the transition beat of a typical MVT cardiac signal. The inputs to the method are a cardiac signal that has been identified as a likely MVT episode, the value of Min for K=1 for that signal ($v_{1f}$), and the value of Min for K=2 for that signal ($v_{2f}$). The system creates S sets of three beats selected from the N beats of the cardiac signal. In one embodiment, the three beats in each set S are sorted by time order: s1, s2 and s3. For each set S, a determination is made of which member of the set s(b) is closest in time to each of the N beats. For each set S, a morphology distance is calculated between s(b) and each N beat and summing those distances to determine a morphology distance sum. Then the morphology distance sums are compared to determine a minimum morphology distance sum (Min) and an associated set S of three beats s1, s2 and s3.

If the value for Min is significantly smaller than $v_{1f}$, $v_{1f}$ is significantly larger than zero and Min is similar in size to $v_{2f}$, then the second beat s2 is the transition beat.

Examples of Episode Data

The cardiac signal has been the primary type of the episode data discussed herein so far. The episode data can include many other types of data in some embodiments. The episode data can include demographic information about the patient, an indication of any therapy that was administered during the episode (such as shock or anti-tachycardia pacing), an indication of the patient's response to any therapy, and information about the patient's condition.

The episode data may also include information from the patient's electronic medical record, device settings at the time of the episode, counter information such as the patient's atrial arrhythmia burden, the patient's drug therapy history, and the patient's ablation history. The patient's ablation history may indicate complete heart block, for example.

In one embodiment, the episode data can include a statement of the device type or device types which generated the data, such as a Holter monitor, pacemaker, single chamber implantable cardioverter defibrillator (ICD), dual chamber ICD, cardiac resynchronization therapy defibrillator (CRT-D) or other devices. Some devices generate an arrhythmia characterization of their own, such as non-sustained ventricular tachy arrhythmia (VT), sustained ventricular tachy arrhythmia, atrial fibrillation (AF) and supraventricular tachycardia (SVT). This device-generated arrhythmia characterization may also be part of the episode data.

It is also possible that the episode data includes caregiver annotations related to the particular arrhythmia episode. Caregiver annotations may include an assigned arrhythmia characterization and many other types of information related to the particular episode.

The episode data can also include electrocardiogram (EGM) recorded before, during and after the duration of the episode. The EGM may be generated by an implanted device. The EGM is an intracardiac EGM in one embodiment.

In one embodiment, the episode data includes both a first and second EGM. The first EGM may be an intracardiac EGM from an implanted device, while the second EGM is a surface EGM from an external device. In one embodiment, both a first and second EGM within the episode data are an intracardiac EGM.

The episode data may also include sensor readings from the patient including physiologic sensors such as a subcutaneous electrogram sensor, pressure sensor, an accelerometer, a temperature sensor and an impedance sensor. Other types of sensor readings that can be included in episode data include readings from a sleep sensor, functional capacity indicator, autonomic tone indicator, sleep quality indicator, cough indicator, anxiety indicator, and cardiovascular wellness indicator for calculating a quality of life indicator quantifying a patient's overall health and well-being. Additional sensor readings that can be included are from a thermometer, a sphygmomanometer or other external devices.

In one embodiment, the episode data also includes pace and sense markers on the EGM, which can indicate when along the course of the EGM the patient's heart rate can be classified in certain ways, such as ventricular tachy arrhythmia (VT), atrial fibrillation (AF) and supraventricular tachycardia (SVT).

In one embodiment, the episode data also includes device diagnostics which are measurements recorded by the device, and which can include average atrial heart rate, average ventricular heart rate and many other measurements.

Sources of Cardiac Signal Data

One example of an episode data-generating device is an implantable cardiac rhythm management device. Specific implantable cardiac rhythm management devices include a pacemaker, a cardioverter-defibrillator, a cardiac resynchronization device, a heart rhythm monitoring device, or the like. Other implantable data-generating devices include pressure sensors, heart sound sensors and impedance sensors. However, it is also possible to generate episode data from external devices, including external pacemakers, external cardioverter-defibrillators, external resynchronization devices, external pressure sensors, external heart sound monitors and external impedance sensors. Additional examples of external devices that monitor cardiac activity include ambulatory electrocardiography devices or Holter monitors, which continuously monitor electrical activity of the heart for 24 hours or more. A data-generating device is one that is capable of providing cardiac signal information about an episode experienced by a particular patient.

Many types of CRM devices communicate with devices located outside of the body, which can receive information from the implanted device including sensor information and information about events, such as when the implanted device has provided therapy. In some cases, the external interface device can also transmit operational parameters to an implanted CRM device, that is, program the device.

These external interface devices can be provided to a patient, often in a patient's home, and can collect information from the implanted device, and provide that information to a computer system designed to monitor the patient's status. An exemplary remote patient management system is the LATITUDE® patient management system, available from Boston Scientific Corporation, Natick, Mass. Aspects of exemplary remote patient management and monitoring systems are described in U.S. Pat. No. 6,978,182, the content of which is herein incorporated by reference in its entirety.

The existence of remote patient management systems such as the LATITUDE® patient management system has provided a large amount of data about patients with implanted medical devices. For example, these systems store patient sensor readings including electrocardiogram (EGM), pressure sensor signals, impedance signals and heart sound signals. The sensor readings can include information associated with arrhythmia episodes and other episodes experienced by the patient. These systems also store information about patient characteristics, device settings and delivery of therapy by the device.

In one embodiment, a system and method uses this storehouse of patient-related data to analyze the device performance, understand a particular patient, understand a patient population group or improve therapy provided by the device. Such a system may operate outside of the device itself, such as on a server that is not at the same location as any of the data-gathering devices. As a result, a large amount of computer processing resources and memory can be devoted to utilizing the patient-related data. For example, an adjudication processor within a patient management system may analyze episode data and provide characterization data about the episodes. Alternatively, such a system and method may operate within a device implanted within a patient to analyze data generated by that patient. For example, a microprocessor within the data-generating device may analyze episode data and provide characterization data.

"Episode" is defined to mean activity of a patient's body within a time period of particular interest. The time period can be a time when there is abnormal activity, for example, abnormal cardiac activity. "Episode data" is defined to include sensor readings from a medical data-generating device before, during and after the episode, and can also include device settings, actions that were taken by the device and other information. According to the system described herein, an episode database stores episode data about episodes that have occurred.

One or more data-generating devices can generate episode data. The episode database may have episode data about a plurality of episodes generated by one device, or generated by multiple devices. In one embodiment, the episode database is external to any of the data-generating devices. However, in another embodiment, the episode database is located within one of the data generating devices.

Storage and Use of the Episode Data and Characterization Data

The episode data or part of the episode data for a particular episode can be analyzed using an adjudication algorithm to determine an episode characterization. For example, an arrhythmia characterization may be determined. The episode characterization data can be stored in an output database. In some embodiments, the characterization data is sent to the data-generating device to be stored. Once an episode characterization has been generated for a particular episode or a group of episodes, then it is possible to provide patients and clinicians with many different types of reports related to the episode data. It is also possible for the system to analyze the characterization data to provide programming recommendations for the data-generating device where certain conditions are present. It is also possible to query the adjudication database for many different types of information that may be useful to clinicians, researchers or regulators.

Description of Hardware Systems

Further detailed embodiments of the hardware of the system will now be described with respect to the attached FIGS.

Figure 10:
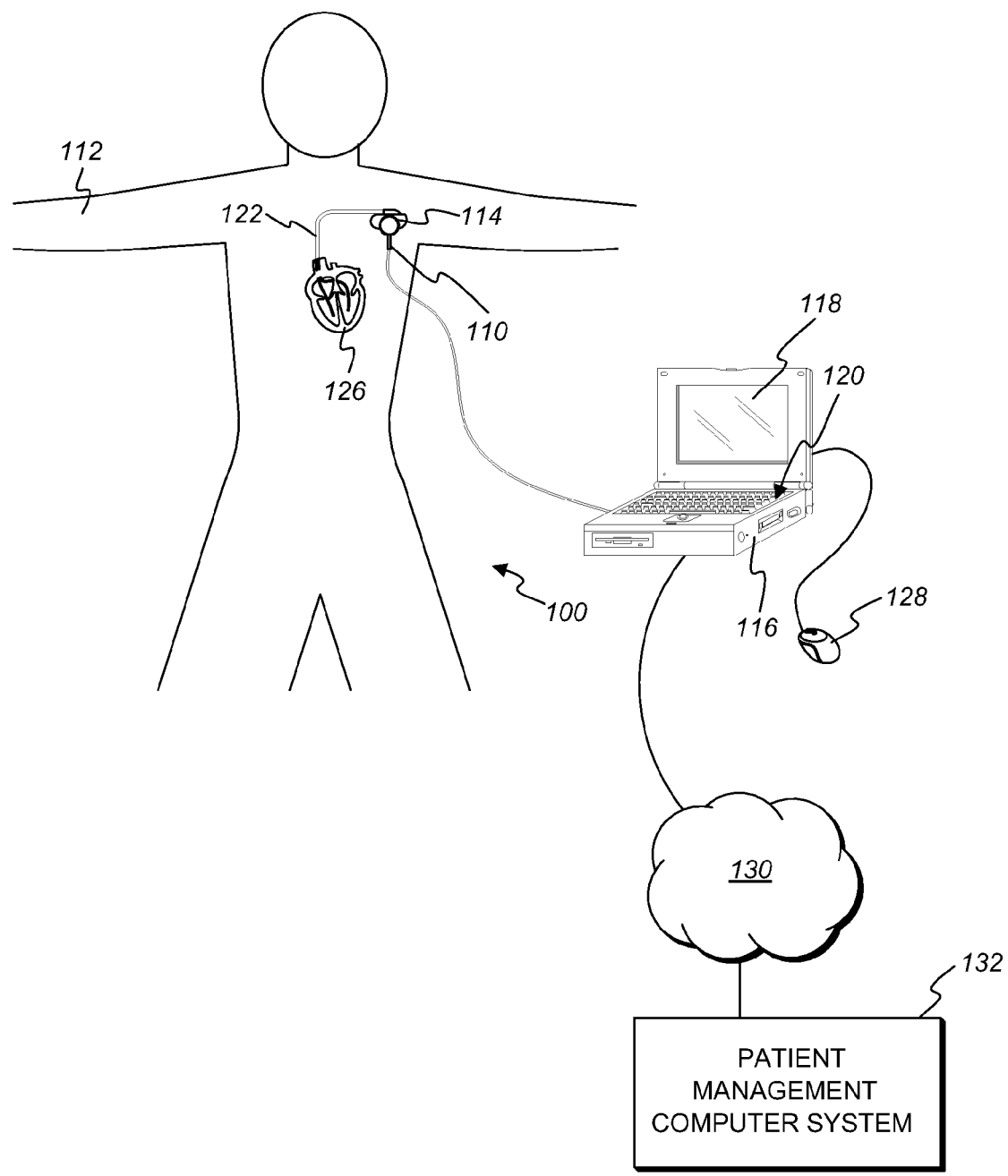
FIG. 10 is a schematic diagram of an exemplary implementation of a cardiac rhythm management (CRM) system, including an implanted CRM device, an external interface device, and a patient management computer system, consistent with at least one embodiment of the invention.

One embodiment of a data-generating device is a CRM device, as will now be described with reference to FIG. 10, which is a schematic of an exemplary CRM system 100. The system 100 can include an implantable medical device 114 disposed within a patient 112. The implantable medical device 114 can include pacing functionality. The implantable medical device 114 can be of various types such as, for example, a pacemaker, a cardioverter-defibrillator, a cardiac resynchronization device, a heart rhythm monitoring device, or the like. In some embodiments, the implantable medical device 114 can include one or more leads 122 disposed in or near the patient's heart 126.

The implantable medical device 114 can be in communication with an external interface system 116. In some embodiments, communication between the implantable medical device 114 and the external interface system 116 can be via inductive communication through a wand 110 held on the outside of the patient 112 near the implantable medical device 114. However, in other embodiments, communication can be carried out via radiofrequency transmission, acoustically, or the like.

The implantable medical device 114 can include one or more implantable sensors in order to gather data regarding the patient 112. For example, the implantable medical device 114 can include an activity level sensor, a respiration sensor, a heart sounds sensor, a blood pressure sensor, an impedance sensor, or other sensors.

The implantable medical device 114 can be configured to store data over a period of time, and periodically communicate with the external interface system 116 in order to transmit some or all of the stored data.

The external interface system 116 can be for example, a programmer, a programmer/recorder/monitor device, a computer, a patient management system, a personal digital assistant (PDA), or the like. As used herein, the term programmer refers to a device that programs implanted devices, records data from implanted devices, and allows monitoring of the implanted device. Exemplary programmer/recorder/monitor devices include the Model 3120 Programmer, available from Boston Scientific Corporation, Natick, Mass. The external interface system 116 can include a user input device, such as a keyboard 120 and/or a mouse 128. The external interface system 116 can include a video output channel and video output device, such as a video display 118 for displaying video output. The displayed video output can include a user interface screen. In addition, the video display 118 can also be equipped with a touch screen, making it into a user input device as well.

The external interface device 116 can display real-time data and/or stored data graphically, such as in charts or graphs, and textually through the user interface screen. In addition, the external interface device 116 can present textual information to a user along with several response options. The external interface device 116 can also input and store a user's response to a question, and can store a user's text response in some embodiments.

In one embodiment, the external interface device 116, which can also be referred to as a user interface, is in communication with a patient management computer system 132. The communication link between the user interface 116 and the patient management computer system 132 may be via phone lines, the Internet 130, or any other data connection. The user interface 116 can also be used when it is not in communication with a device, but is only in communication with the patient management computer system 132.

In one embodiment, the external interface device 116 is capable of changing the operational parameters of the implantable medical device 114, and is therefore referred to as a programmer. Typically, programmers are used to interface with CRM devices in a clinic or hospital setting. In this context, the user of the external interface device is a physician or trained technician.

Figure 11:
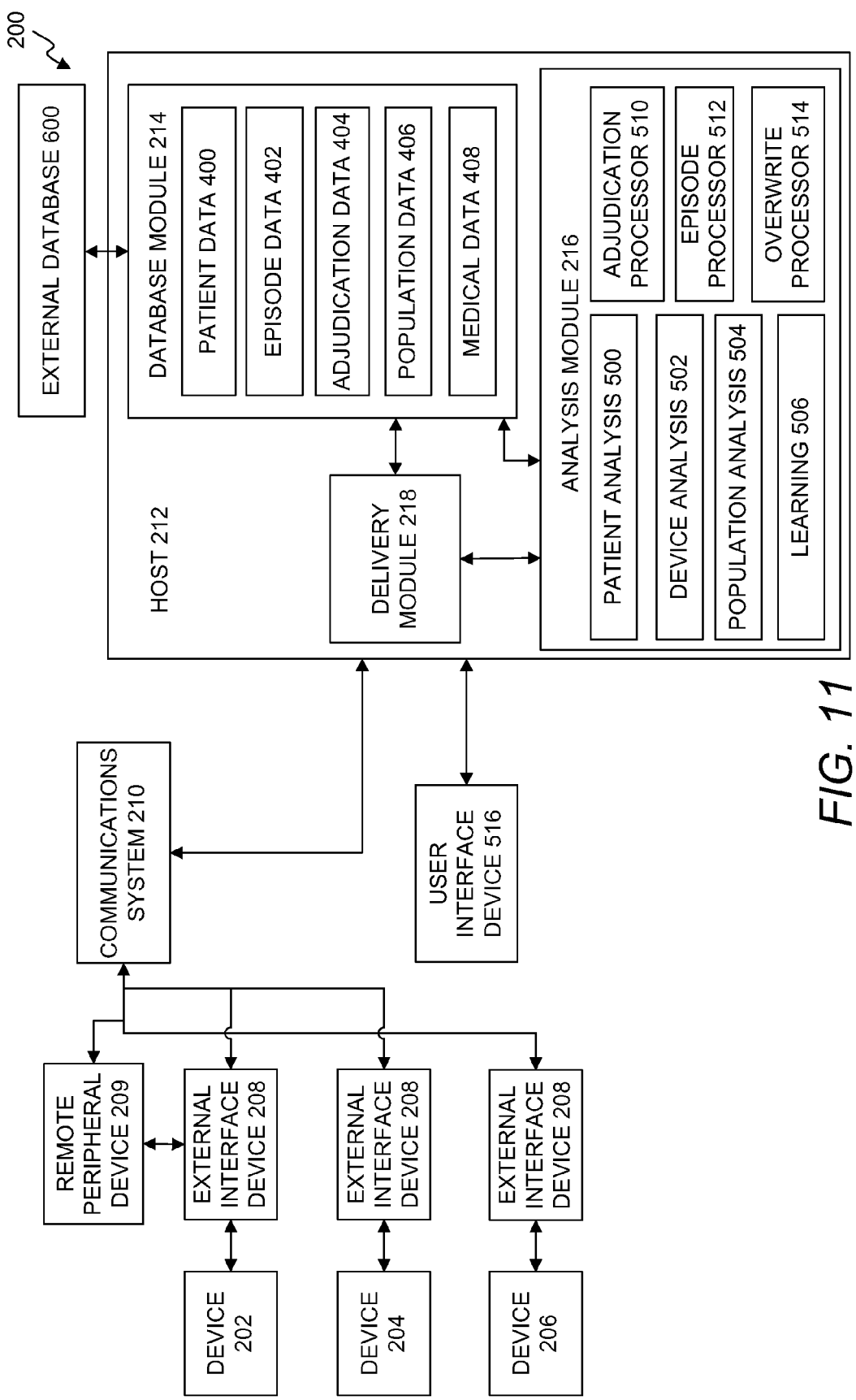
FIG. 11 is a schematic illustration of a patient management system consistent with at least one embodiment of the invention.

FIG. 11 is a schematic illustration of a patient management system consistent with at least one embodiment of the invention. The patient management system is capable of maintaining an episode database using computer storage medium. Of note, the episode database may also be present in an implantable or implanted device as discussed further herein. A computer storage medium is any technology, including devices and materials, used to place, keep and retrieve data. Examples of computer storage medium include random-access memory (RAM), a network-attached storage device, magnetic storage such as hard disk drives, optical discs, and a redundant array of independent discs (RAID). Patient management system 200 generally includes one or more devices 202, 204, and 206, one or more external interface devices 208, a communication system 210, one or more remote peripheral devices 209, and a host 212.

Each component of the patient management system 200 can communicate using the communication system 210. Some components may also communicate directly with one another. The various components of the example patient management system 200 illustrated herein are described below.

Data-generating devices 202, 204, and 206 can be implantable devices or external devices that may provide one or more of the following functions with respect to a patient: (1) sensing, (2) data analysis, and (3) therapy. For example, in one embodiment, devices 202, 204, and 206 are either implanted or external devices used to measure a variety of physiological, subjective, and environmental conditions of a patient using electrical, mechanical, and/or chemical means. The devices 202, 204, and 206 can be configured to automatically gather data or can require manual intervention by the patient or another person. The devices 202, 204, and 206 can be configured to store data related to the physiological and/or subjective measurements and/or transmit the data to the communication system 210 using a variety of methods, described in detail below. Although three devices 202, 204, and 206 are illustrated in the example embodiment shown, many more devices can be coupled to the patient management system. In one embodiment, each of the devices 202, 204 and 206 is serving a different patient. In one embodiment, two or more devices are serving a single patient.

The devices 202, 204, and 206 can be configured to analyze the measured data and act upon the analyzed data. For example, the devices 202, 204, and 206 can be configured to modify therapy or provide an alarm based on the analysis of the data.

In one embodiment, devices 202, 204, and 206 provide therapy. Therapy can be provided automatically or in response to an external communication. Devices 202, 204, and 206 are programmable in that the characteristics of their sensing, therapy (e.g., duration and interval), or communication can be altered by communication between the devices 202, 204, and 206 and other components of the patient management system 200. Devices 202, 204, and 206 can also perform self-checks or be interrogated by the communication system 210 to verify that the devices are functioning properly. Examples of different embodiments of the devices 202, 204, and 206 are provided herein.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance. Derived measurements can also be determined from the implantable device sensors (e.g., a sleep sensor, functional capacity indicator, autonomic tone indicator, sleep quality indicator, cough indicator, anxiety indicator, and cardiovascular wellness indicator for calculating a quality of life indicator quantifying a patient's overall health and well-being).

Devices 202, 204, and 206 can also be external devices, or devices that are not implanted in the human body, that are used to measure physiological data (e.g., a thermometer, sphygmomanometer, or external devices used to measure blood characteristics, body weight, physical strength, mental acuity, diet, heart characteristics, and relative geographic position).

The patient management system 200 may also include one or more remote peripheral devices 209 (e.g., cellular telephones, pagers, PDA devices, facsimiles, remote computers, printers, video and/or audio devices) that use wired or wireless technologies to communicate with the communication system 210 and/or the host 212.

The example database module 214 includes a patient database 400, an episode database 402, an adjudication database 404, a population database 406, and a medical database 408, all of which are described further below. The patient database 400 includes patient specific data, including data acquired by the devices 202, 204, and 206, as well as a patient's medical records and historical information. The population database 406 includes non-patient specific data, such as data relating to other patients and population trends. The example medical database 408 includes clinical data relating to the treatment of diseases, such as historical trend data for multiple patients in the form of a record of progression of their disease(s) along with markers of key events.

The episode database 402 has episode data regarding a plurality of different episodes generated from those of devices 202, 204, and 206 that provide episode data. The adjudication database 404 includes adjudication conclusions associated with the episode data such as arrhythmia episodes. The adjudication database 404 and the episode database 402 can actually be a single database with shared data that is used as either episode data or adjudication data depending on the particular data set being presented to the user.

Information can also be provided from an external source, such as external database 600. For example, the external database 600 could include external medical records maintained by a third party, such as drug prescription records maintained by a pharmacy, providing information regarding the type of drugs that have been prescribed for a patient or, in another example, authorization data from patient groups that have authorized users to view arrhythmia episode data.

The example analysis module 216 includes a patient analysis module 500, device analysis module 502, population analysis module 504, and a learning module 506. Patient analysis module 500 may utilize information collected by the patient management system 200, as well as information for other relevant sources, to analyze data related to a patient and provide timely and predictive assessments of the patient's well-being. Device analysis module 502 analyzes data from the devices 202, 204, and 206 and external interface devices 208 to predict and determine device issues or failures. Population analysis module 504 uses the data collected in the database module 214 to manage the health of a population. Learning module 506 analyzes the data provided from the various information sources, including the data collected by the patient system 200 and external information sources, and may be implemented via a neural network (or equivalent) system to perform, for example, probabilistic calculations.

The analysis module 216 further includes an adjudication processor 510, and episode processor 512 and an overwrite processor 514. In one embodiment, the adjudication processor is operatively connected to at least the episode database 402 and is configured to receive as input episode data regarding one of the different arrhythmia episodes. The adjudication processor uses an automated method or algorithm to generate characterization data about the arrhythmia episode. The characterization data, which may include an arrhythmia characterization for each arrhythmia episode that is analyzed, is stored in the adjudication database 404.

The episode processor 512 performs processing of the adjudication database such as in order to provide reports, patient alerts, or programming recommendations. The overwrite processor 514 can analyze data provided from the episode database 402, the adjudication database 404, and other portions of the patient management system 200 to determine what particular portion of episode data for one of the arrhythmia episodes from the episode database should be displayed to a user. Overwrite processor 514 can, through the delivery module 218 described below, provide the means for graphically displaying a portion of data selected from arrhythmia episode data related to an arrhythmia episode of a patient, such as data generated by a data-generating device and stored in the episode database.

Overwrite processor 514 also requests from a user any changes in the characterization data determined by the adjudication processor, and can articulate the request for user input characterizing an arrhythmia episode. The request may be a direct question to a user, a series of choices provided to the user, or simply a blank space on the user interface configured to accommodate the user input. The overwrite processor 514 may also store the overwrite history for individual users.

One or more portions of the analysis module 216, such as the adjudication processor 510 and episode processor 512, may be located remotely from other parts of the patient management system 200. A microprocessor of a data-generating device may also serve as an adjudication processor in some embodiments.

Delivery module 218 coordinates the delivery of reports, patient alerts or programming recommendations based on the analysis performed by the host 212. For example, based on the data collected from the devices and analyzed by the host 212, the delivery module 218 can deliver information to the caregiver, user, or to the patient using, for example, a display provided on the external interface device 208. A user interface device 516 that is independent of a data-generating device may also be used to deliver information. The external interface device 208 and user interface device 516 are also configured, according to multiple embodiments, to display a report, alert, or programming recommendation, receive overwrite information from a user, and receive other data from the user. Displayed data, as described above, can be determined by the episode processor 512, overwrite processor 514 and delivery module 218.

Figure 12:
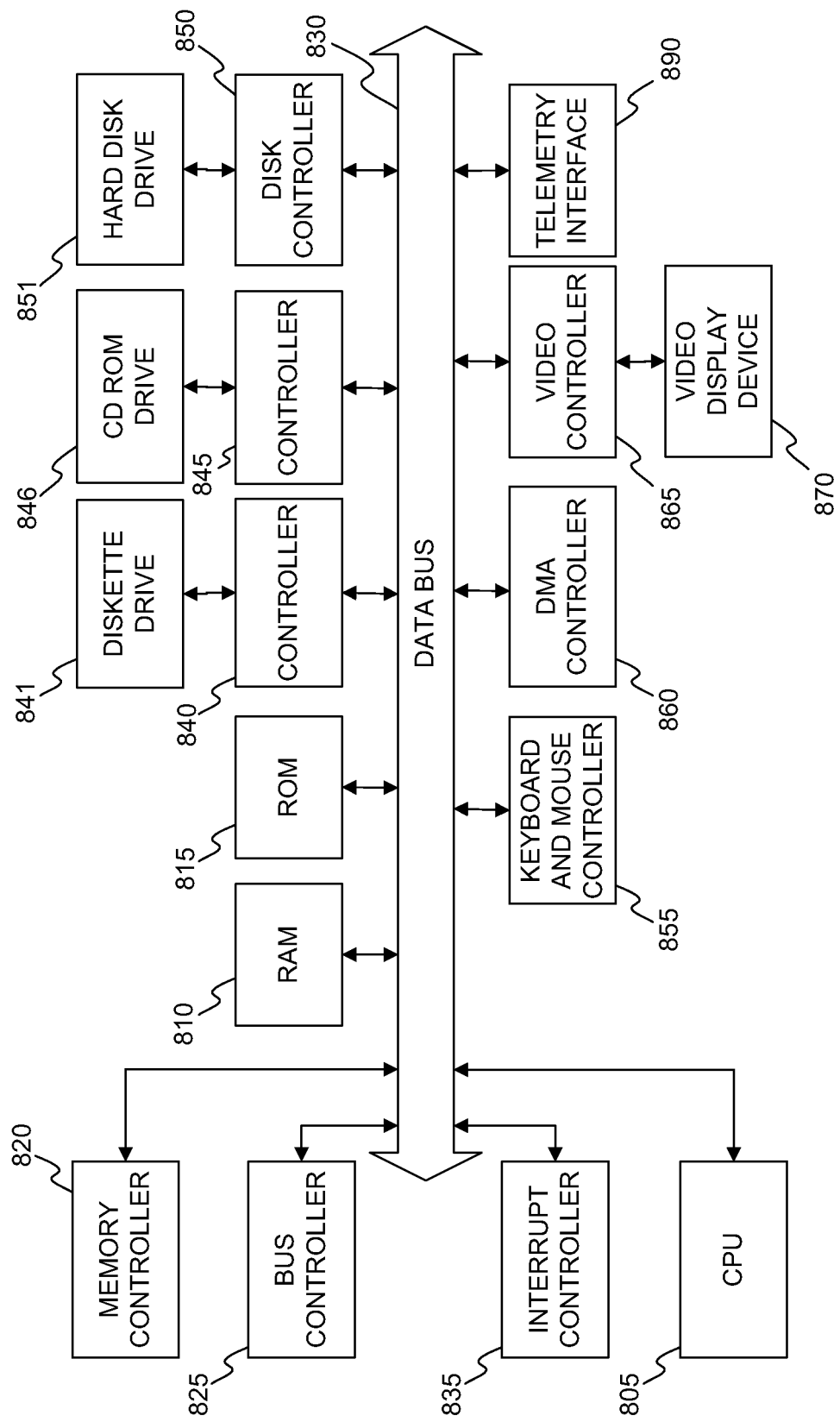
FIG. 12 is a schematic diagram of an implementation of the components of an external interface device such as a programmer, in accordance with various embodiments.

External interface devices 208 to display information, such as programmer/recorder/monitors, can include components common to many computing devices. User interface devices 516 to display and received information from users can also include components common to many computing devices. Referring now to FIG. 12, a diagram of various components is shown in accordance with some embodiments of the invention. However, it is not required that an external interface device have all of the components illustrated in FIG. 12.

In one embodiment, the external interface device includes a central processing unit (CPU) 805 or processor, which may include a conventional microprocessor, random access memory (RAM) 810 for temporary storage of information, and read only memory (ROM) 815 for permanent storage of information. A memory controller 820 is provided for controlling system RAM 810. A bus controller 825 is provided for controlling data bus 830, and an interrupt controller 835 is used for receiving and processing various interrupt signals from the other system components.

Mass storage can be provided by diskette drive 841, which is connected to bus 830 by controller 840, CD-ROM drive 846, which is connected to bus 830 by controller 845, and hard disk drive 851, which is connected to bus 830 by controller 850. User input to the programmer system may be provided by a number of devices. For example, a keyboard and mouse can connected to bus 830 by keyboard and mouse controller 855. DMA controller 860 is provided for performing direct memory access to system RAM 810. A visual display is generated by a video controller 865 or video output, which controls video display 870. The external system can also include a telemetry interface 890 or telemetry circuit which allows the external system to interface and exchange data with an implantable medical device. It will be appreciated that some embodiments may lack various elements illustrated in FIG. 12.

Figure 13:
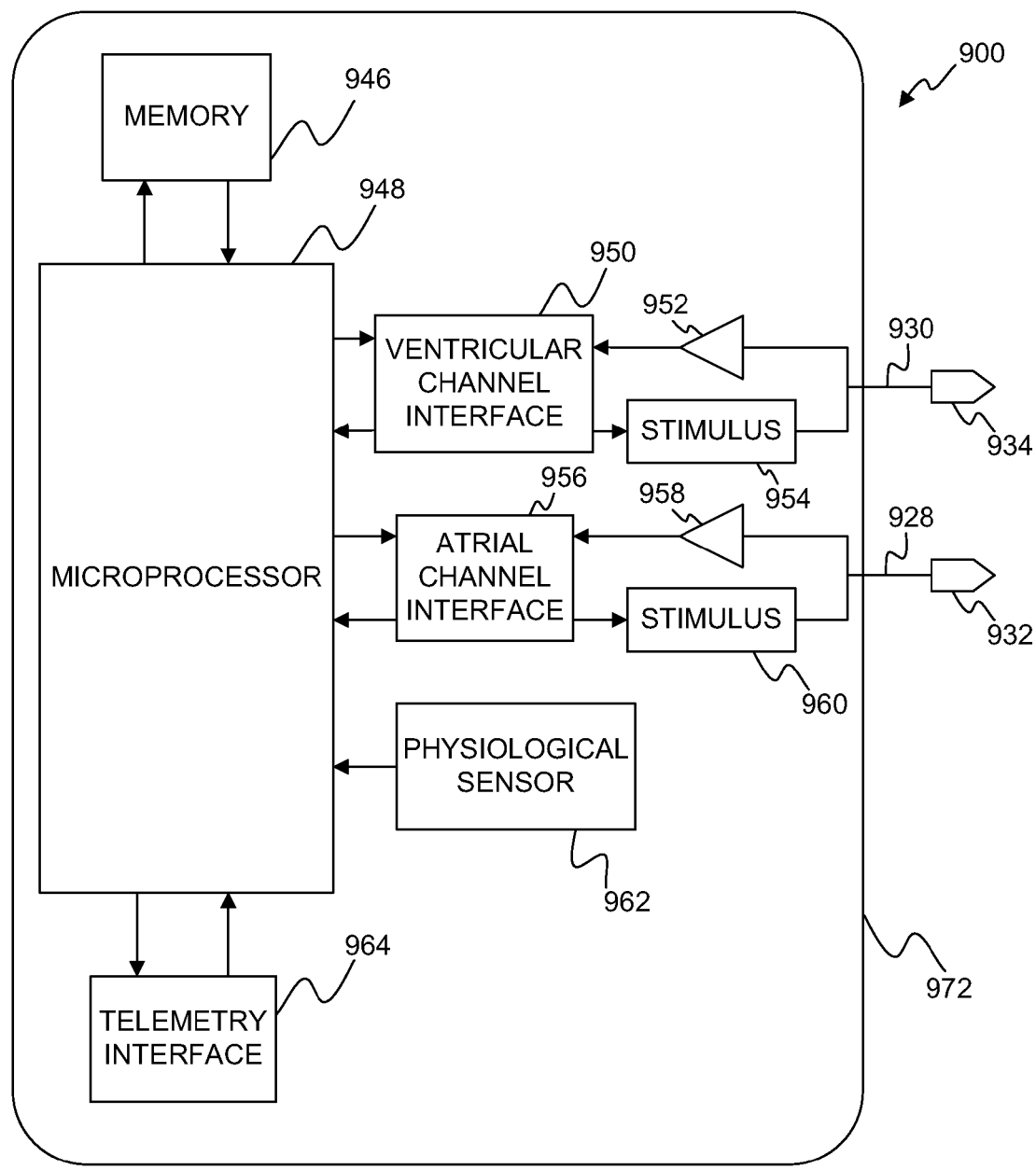
FIG. 13 is a schematic view of components of one example of a data-generating device in accordance with an embodiment of the invention.

Referring now to FIG. 13, some components of an exemplary implantable system 900 are schematically illustrated. The implantable medical system 900 can include an implantable medical device 972 coupled to one or more stimulation leads 930 and 928. The implantable device 972 can also include one or more physiological sensors 962, or other sensors, such as a pressure sensor, impedance sensor and others.

The implantable device can include a microprocessor 948 (or processor) that communicates with a memory 946 via a bidirectional data bus. The memory 946 (a type of computer storage medium) typically comprises ROM or RAM for program storage and RAM for data storage. The implantable device is a computer system and can be configured to execute various operations such as processing of signals and execution of methods for automatically analyzing a cardiac signal, as described herein. The methods described herein can be implemented in an implanted device for real-time rhythm analysis and discrimination. A telemetry interface 964 is also provided for communicating with an external unit, such as a programmer device or a patient management system.

The implantable device can include ventricular sensing and pacing channels comprising sensing amplifier 952, output circuit 954, and a ventricular channel interface 950 which communicates bi-directionally with a port of microprocessor 948. The ventricular sensing and pacing channel can be in communication with stimulation lead 930 and electrode 934. The implantable device can include atrial sensing and pacing channels comprising sensing amplifier 958, output circuit 960, and an atrial channel interface 956 which communicates bi-directionally with a port of microprocessor 948. The atrial sensing and pacing channel can be in communication with stimulation lead 928 and electrode 932. For each channel, the same lead and electrode can be used for both sensing and pacing. The channel interfaces 950 and 956 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A method for automatically analyzing a cardiac signal comprising the steps of:
    i) providing an episode database on a computer system including at least one episode data record, wherein each episode data record includes a cardiac signal from at least one data-generating device, wherein the cardiac signal has N beats;
    ii) selecting a range of possible values for K;
    iii) for each value of K, performing the following steps using a computer system:
        (a) for each set S of K beats, perform the following steps:
            1. for each beat b not in Set S, find which member s(b) of the set S is closest to b and calculate a morphology distance between s(b) and b;
            2. for each beat b, calculate a morphology distance compilation value for each set S, wherein the morphology distances are used in calculating the morphology distance compilation value;
        (b) compare the morphology distance compilation values to identify which set S of K beats results in the best representation of the cardiac signal based on the morphology distance compilation value; and (c) record the set s of K beats that results in the best representation of the cardiac signal as a beat template for the value of K and record the morphology distance compilation value for the beat template;

iv) based on the morphology distance compilation values for each value of K, determine a best value of K for the cardiac signal where K beat templates can represent all the beats in the cardiac signal; and v) output the best value of K for the cardiac signal.

2. The method of claim 1 further comprising the step of:
assigning an episode characterization for each episode data record based at least partially on the value K and how well the episode is represented by K beat templates.

3. The method of claim 2 wherein the episode characterization is an arrhythmia episode characterization.

4. The method of claim 3 wherein the arrhythmia characterization is selected from a group comprising at least polymorphic ventricular tachycardia (PVT/VF), monomorphic ventricular tachycardia (MVT), atrial fibrillation (AF), and other supraventricular tachycardia (other SVT).

5. The method of claim 1 wherein the morphology distance is selected from a group comprising at least Euclidean distance, Mahalanobis distance, and Manhattan distance.

6. The method of claim 1 wherein:
calculating the morphology distance compilation value for each set S of K beats comprises summing the morphology distances between each beat in the set S and each beat b not in Set S in the cardiac signal to calculate a morphology distance sum, and recording the set S of K beats that results in the best representation of the cardiac signal as a beat template for the value of K comprises recording the set S of K beats with a lowest morphology distance sum.

7. The method of claim 1
wherein each beat comprises multiple channels of the cardiac signal, and wherein the morphology distance is based on a channel morphology distance for each channel and a beat length difference.

8. The method of claim 1 wherein for a particular cardiac signal, K beat templates are presented to a user on a display device to represent the signal morphology of the particular cardiac signal.

9. The method of claim 1 wherein for a particular cardiac signal, M beat templates are presented to a user on a display device to represent the signal morphology of the particular cardiac signal, where M is less than K.

10. A system for automatically analyzing a cardiac signal, comprising:

an episode database including a plurality of episode data records of one or more patients, wherein each episode data record includes a cardiac signal having N beats from at least one data-generating device;

an adjudication processor configured to:
i) for each value of K in a range of possible values of K, perform the following steps:
(a) for each set S of K beats in the cardiac signal, perform the following steps:
1. for each beat b not in Set S, find which member s(b) of the set S is closest to b and calculate a morphology distance between s(b) and b;
2. for each beat b, calculate a morphology distance compilation value for each set S, wherein the morphology distances are used in calculating the morphology distance compilation value;
(b) compare the morphology distance compilation values to identify which set S of K beats results in the best representation of the cardiac signal based on the morphology distance compilation value; and
(c) record the set s of K beats that results in the best representation of the cardiac signal as a beat template for the value of K and record the morphology distance compilation value for the beat template; and ii) based on the morphology distance compilation values for each value of K, determine a best value of K for the cardiac signal where K beat templates can represent all the beats in the cardiac signal; and an output database comprising a best value of K for the cardiac signal.

11. The system of claim 10 wherein the output database further comprises an episode characterization for each episode data record that is determined by the adjudication processor based at least partially on the value K.

12. The system of claim 11 wherein the episode characterization is an arrhythmia episode characterization.

13. The system of claim 12 wherein the arrhythmia characterization is selected from a group comprising at least polymorphic ventricular tachycardia (PVT/VF), monomorphic ventricular tachycardia (MVT), atrial fibrillation (AF),and other supraventricular tachycardia (other SVT).

14. The system of claim 10 wherein the morphology distance is selected from a group comprising at least Euclidean distance, Mahalanobis distance, and Manhattan distance.

15. The system of claim 10 further comprising a display device, wherein for a particular cardiac signal, K beat templates are presented to a user on the display device to represent the signal morphology of the particular cardiac signal.

* * * * *